(12) United States Patent
Shin et al.

(10) Patent No.: US 10,893,719 B2
(45) Date of Patent: Jan. 19, 2021

(54) SMART SHOE MODULE

(71) Applicant: LG ELECTRONICS INC., Seoul (KR)

(72) Inventors: Seungyong Shin, Seoul (KR); Kyoungtae Kim, Seoul (KR); Minsoo Kim, Seoul (KR); Jeonghwa Kim, Seoul (KR); Kuangjun An, Seoul (KR); Sungkwon Jang, Seoul (KR); Jinho Cho, Seoul (KR); Donghoon Han, Seoul (KR); Changkyu Hwang, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 238 days.

(21) Appl. No.: 16/082,820

(22) PCT Filed: Mar. 16, 2017

(86) PCT No.: PCT/KR2017/002839
§ 371 (c)(1),
(2) Date: Sep. 6, 2018

(87) PCT Pub. No.: WO2017/160096
PCT Pub. Date: Sep. 21, 2017

(65) Prior Publication Data
US 2019/0082771 A1 Mar. 21, 2019

(30) Foreign Application Priority Data

Mar. 17, 2016 (KR) .................. 10-2016-0031880
Apr. 28, 2016 (KR) .................. 10-2016-0052370

(51) Int. Cl.
*A43B 3/00* (2006.01)
*G01L 1/14* (2006.01)
(Continued)

(52) U.S. Cl.
CPC .............. *A43B 3/0005* (2013.01); *A43B 3/00* (2013.01); *A61B 5/6807* (2013.01); *G01L 1/142* (2013.01);
(Continued)

(58) Field of Classification Search
CPC . A43B 3/00; A43B 3/0005; A61B 2560/0214; A61B 2560/0412;
(Continued)

(56) References Cited

U.S. PATENT DOCUMENTS 5,815,955 A * 10/1998 Wu ...................... A43B 1/0036
36/137
10,159,427 B2 * 12/2018 Malawey ............. A61B 5/7455
(Continued)

FOREIGN PATENT DOCUMENTS

CN 106356229 A * 1/2017 ............. H01H 13/14
JP 6-52508 U 7/1994
(Continued)

*Primary Examiner* — Francis C Gray
(74) *Attorney, Agent, or Firm* — Birch, Stewart, Kolasch & Birch, LLP

(57) ABSTRACT

Provided in a smart shoe module mounted to a smart shoe for analyzing the motion of a wearer and providing various functions, the smart shoe module comprising: an upper case which forms an upper outer experience of a pressure switch and elastically behaves by means of a pressure, which is applied in a first direction and has a particular value or larger, in order to accurately measure the motion of the wearer by measuring the pressure generated during walking of a wearer, as digital signals such as on-signal and an off-signal, and, moreover, minimize a manufacturing tolerance so as to prevent an error in distinguishing between an on-signal and an off-signal from being caused by the pressure generated during walking of the wearer; a lower case coupled to the lower end of the upper case and forming a lower end outer experience of the pressure switch; a sub-
(Continued)

stance amounted to the inside of the upper case and generating a signal in the first circuit unit through the elastic behavior; and a control unit for processing the signal generated in the first circuit unit.

18 Claims, 19 Drawing Sheets

(51) Int. Cl.
*G01L 1/16* (2006.01)
*A61B 5/00* (2006.01)
*G01L 1/18* (2006.01)
*G01L 1/22* (2006.01)
*G01L 5/00* (2006.01)
*A61B 5/11* (2006.01)

(52) U.S. Cl.
CPC .................. *G01L 1/16* (2013.01); *G01L 1/18* (2013.01); *G01L 1/2287* (2013.01); *G01L 5/0052* (2013.01); *A61B 5/1118* (2013.01); *A61B 2560/0214* (2013.01); *A61B 2560/0412* (2013.01); *A61B 2562/0219* (2013.01); *A61B 2562/0247* (2013.01)

(58) Field of Classification Search
CPC .... A61B 2562/0219; A61B 2562/0247; A61B 5/1118; A61B 5/6807; G01L 1/142; G01L 1/16; G01L 1/18; G01L 1/2287; G01L 5/0052
See application file for complete search history.

(56) References Cited

U.S. PATENT DOCUMENTS

| | | | |
|---|---|---|---|
| 2008/0203144 A1* | 8/2008 | Kim | A61B 5/1118 235/105 |
| 2013/0247424 A1* | 9/2013 | Tseng | A43B 3/0005 36/136 |
| 2015/0359457 A1* | 12/2015 | Blumenthal | A61B 5/02444 73/172 |
| 2017/0213095 A1* | 7/2017 | Li | A61B 5/117 |
| 2019/0281919 A1* | 9/2019 | Chen | H01R 13/6675 |

FOREIGN PATENT DOCUMENTS

| KR | 10-0987273 B1 | 10/2010 |
|---|---|---|
| KR | 10-2015-0048019 A | 5/2015 |
| KR | 10-1583369 B1 | 1/2016 |

\* cited by examiner (a)

(b)

| | | Left smart shoe | Right smart shoe |
|---|---|---|---|
| Measurement | Pressure sensor | 0.9 | 1.1 |
| | Motion sensor | 0.8 | 1.2 |

| | Calibration algorithm |
|---|---|
| Left smart shoe value (A) measured by the pressure sensor | A * 0.8/0.9 |
| Left smart shoe value (B) measured by the pressure sensor | B * 1.2/1.1 |

SMART SHOE MODULE

CROSS REFERENCE TO RELATED APPLICATIONS

This application is the National Phase of PCT International Application No. PCT/KR2017/002839, filed on Mar. 16, 2017, which claims priority under 35 U.S.C. 119(a) to Patent Application Nos. 10-2016-0031880, filed in the Republic of Korea on Mar. 17, 2016, and 10-2016-0052370, filed in the Republic of Korea on Apr. 28, 2016, all of which are hereby expressly incorporated by reference into the present application.

FIELD

Embodiments of the present disclosure relate to a smart shoe module provided in a smart shoe and configured to perform diverse functions.

BACKGROUND

Recently, mobile terminals become realized as smart terminals configured to perform the functions related with production and consumption of contents after developing from past communication functions such as multimedia players having combined functions.

Such smart terminals have been expanded diverse objects as well as conventional mobile terminals so as to perform diverse functions for objects independently or via interworking between smart terminals or objects.

Especially, such a smart terminal is extensively applicable even to an object which is wearable on a user, in other words, a wearable device.

Examples of the wearable device may include from a smartwatch, a smart glass and a head mounted display (HMD) even to indispensable goods which users have to wear such as clothes and shoes.

Shoes as a wearable device, in other words, smart shoes are configured to perform a function of informing a user via a smart terminal such as a mobile terminal or autonomously by analyzing information about the user's or wearer's activities.

More specifically, a smart shoe may perform functions of detecting, sensing or recording the activity time, activity distance, and activity locus while the wearer or user is wearing the smart shoe.

A motion sensor is used in measuring the location of the smart shoe on a 2-dimensional or 3-dimensional space such as the wearer's activity distance or locus.

Such a motion sensor is able to figure out not only an approximate location by using Global Positioning System (GPS) but also a specific location by using an acceleration sensor and a gyro sensor.

Moreover, the motion sensor may measure the speed of the smart shoes and calculate whether the wearer is walking or a standard of walk units.

In this instance, the motion sensor has to maintain a state of measuring the location of the smart shoes consistently, in other words, an electricity consuming state. Because of that, the smart shoes have a disadvantage of large battery consumption and an accompanying disadvantage in reducing the overall weight of the smart shoes.

In addition, when the wearer's activity locus is detected by using only a conventional motion sensor, the noise generated in the sensor could result in failure to identify the wearer's walks precisely such that a cumulative error might occur. In other words, the standard of the wearer's walk units is calculated wrongly enough to generate a problem in measuring the records.

Accordingly, the pressure generated by the wearer'walking is measured and converted into a digital signal such as an On-signal or an Off-signal so as to measure the wearer's motion precisely.

The electrical connection between a conductive member and a first circuit unit to generate the On-signal may be facilitated in diverse ways and the shape and properties of the conductive member may expect various additive effects.

DETAILED DESCRIPTION OF THE INVENTION

Technical Problem

To overcome the disadvantages, an object of the present invention is to address the above-noted and other problems and to detect a smart-shoe wearer's motion precisely.

Another object of the present invention is to minimize the power consumption in detecting the wearer's motion.

A further object of the present invention is to clearly distinguish the On-signal or Off-signal generated in a smart shoe module configured to figure out the wearer's motion.

Technical Solution

To achieve these objects and other advantages and in accordance with the purpose of the embodiments, as embodied and broadly described herein, a smart shoe module comprising: an upper case provided to define an upper exterior of a pressure switch and configured to be elastically movable by a specific pressure value or more activating in a first direction; a lower case coupled to a lower end of the upper case and provided to define a lower end exterior of the pressure switch; a circuit board loaded in the lower case and comprising a first circuit unit; a conductive member provided between the upper and the first circuit unit of the circuit board and configured to generate a signal in the first circuit unit according to the elastic motion; and a controller implemented to process the signal generated in the first circuit unit.

The first circuit unit and the conductive member may form a first gap.

The smart shoe module may further comprise a coupling hole provided in a predetermined area of one of the upper and lower cases; a coupling projection provided in a predetermined area of the other one and configured to be fitted to the coupling hole; and a support rib projected from an inner surface of the upper case and configured to support the first circuit unit; wherein a second gap is formed between the coupling hole and the coupling projection, and the support rib and the first circuit unit contacts with each other.

A third gap may be formed in an outer boundary area of the coupling between the upper and the lower case.

The smart shoe module may further comprise a hook portion provided in the inner surface of the lower case and configured to fix the circuit board.

The smart shoe module may further comprise an adhesive tape provided between the conductive member and the upper case.

The conductive member may be formed in the inner surface of the upper case by double-injection molding.

The smart shoe module may further comprise a recess portion formed in the inner case of the upper case, corresponding to the conductive member.

The conductive member may comprise at least one of a variable resistance element, a dielectric material and a dome cap.

The smart shoe module may further comprise a conductive layer configured to cover at least predetermined area of an upper surface of the variable resistance element, when the conductive member is the variable resistance element.

Embodiments of the present invention also provide a smart shoe module comprising: an upper case provided to define an upper exterior of a pressure switch and configured to be elastically movable by a specific pressure value or more activating in a first direction; a lower case coupled to a lower end of the upper case and provided to define a lower end exterior of the pressure switch; a circuit board loaded in the lower case and comprising a first circuit unit; a piezo element provided between the upper and the first circuit unit of the circuit board and configured to generate a signal in the first circuit unit according to the elastic motion; and a controller implemented to process the signal generated in the first circuit unit.

The controller may calculate a user's momentum based on a voltage of a signal generated in the first circuit unit.

The smart shoe module may further comprise a power supply unit configured to be supplied the electricity generated in the piezo element and have the electricity accumulative therein.

The smart shoe module may further comprise a power supply unit configured to apply a voltage to the piezo element, wherein the controller controls the power supply unit to apply a corresponding voltage to a control signal preset in the piezo element.

The preset control signal may be configured to vary at least one of the applied voltage size, frequency and period.

The smart shoe module may further comprise a location information module configured to measure or transmit location information about the smart shoe module, wherein the controller varies the period of the applied voltage in response to the location information measured by the location information module and a distance with a specific location.

The smart shoe module may comprise a left smart shoe module and a right smart shoe module which include the piezo elements, respectively, wherein the preset control signal comprises a first control signal configured to apply a voltage to one of the piezo elements; a second control signal configured to apply voltages to both of the piezo element; and a third control signal configured to alternately apply voltages to the piezo elements.

Embodiments of the present invention may a smart shoe module system comprising: a left smart shoe module and a right smart module, wherein each of the left and right smart shoe modules comprises an upper case provided to define an upper exterior of a pressure switch and configured to be elastically movable by a specific pressure value or more activating in a first direction; a lower case coupled to a lower end of the upper case and provided to define a lower end exterior of the pressure switch; a circuit board loaded in the lower case and comprising a first circuit unit; a conductive member configured to form a first gap in the upper case, together with the first circuit unit, and generate a signal in the first circuit unit according to the elastic motion; a motion sensor comprising an acceleration sensor and a gyro sensor; and a controller implemented to process the signal generated in the first circuit unit, wherein the controller configured to calibrate a rate of the on-signals measured by the first circuit unit provided in each of the left and right smart shoe modules based on a rate of the ground supporting time analyzed by each of the motion sensors, based on a calibrated on-signal rate.

The controller may activate the motion sensor which is in inactivated state, when performing the calibration.

The controller may perform the calibration at preset intervals or intervals set by the user.

Advantageous Effects

As described above, the smart shoes in accordance with the present disclosure may have following effects.

According to the embodiments of the present disclosure, noise may be minimized by using the acceleration sensor or the gyro sensor in analyzing the wearer's motion.

Furthermore, power consumption may be minimized by using the acceleration sensor or the gyro sensor in the smart shoe module.

Still further, the contact reliability of the contact structure facilitated by the pressure generated by the wearer so as to distinguish the on-signal and the off-signal from each other.

Further scope of applicability of the present invention will become apparent from the detailed description given hereinafter. However, it should be understood that the detailed description and specific examples, while indicating preferred embodiments of the invention, are given by illustration only, since various changes and modifications within the spirit and scope of the invention will become apparent to those skilled in the art from this detailed description.

DESCRIPTION OF BEST EMBODIMENTS

Figure 1:
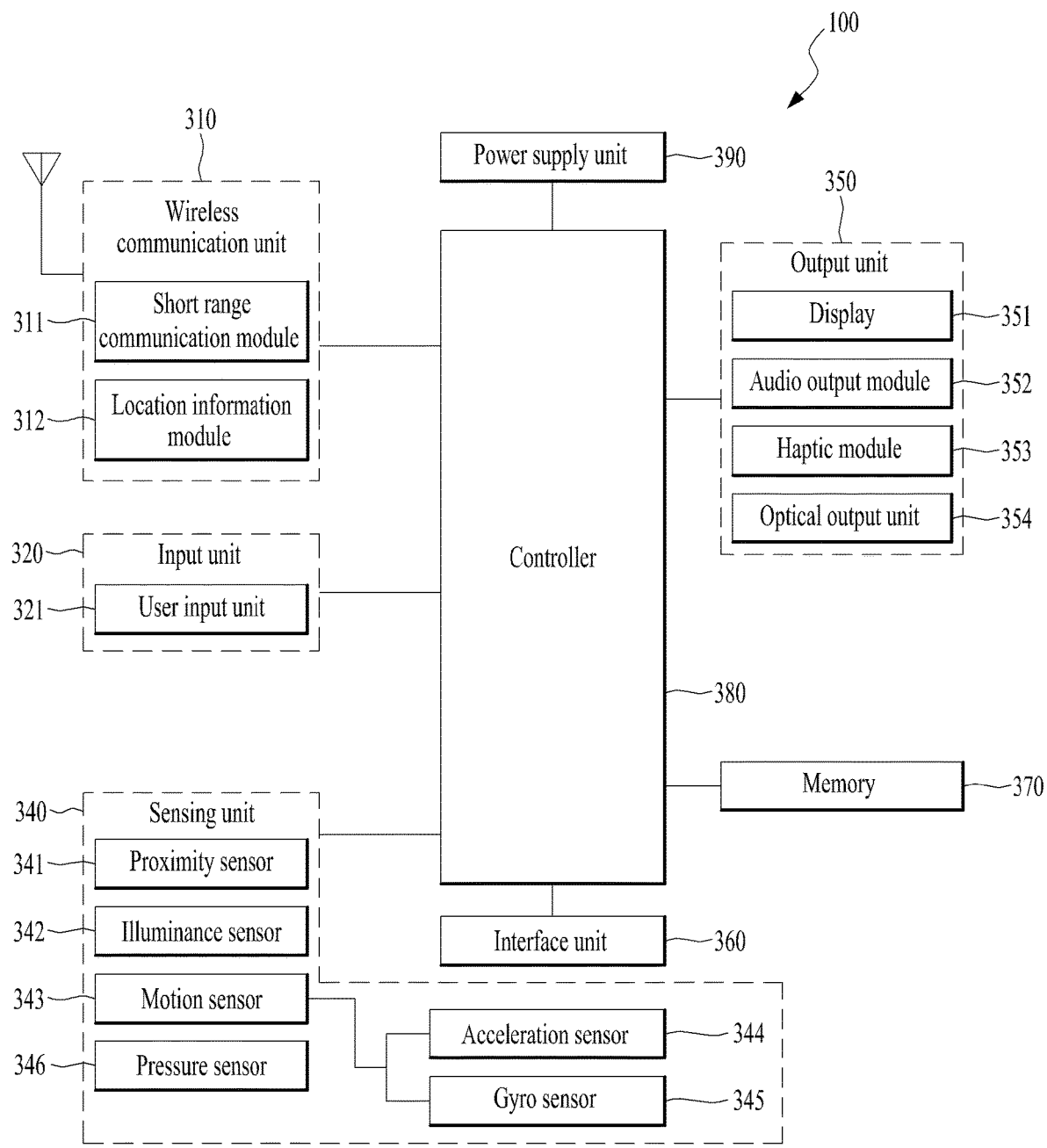
FIG. 1 is a block diagram to describe a smart shoe module in accordance with the present invention.

Description will now be given in detail according to exemplary embodiments disclosed herein, with reference to the accompanying drawings. For the sake of brief description with reference to the drawings, the same or equivalent components may be provided with the same reference numbers, and description thereof will not be repeated. In general, a suffix such as "module" and "unit" may be used to refer to elements or components. Use of such a suffix herein is merely intended to facilitate description of the specification, and the suffix itself is not intended to give any special meaning or function. In the present disclosure, that which is well-known to one of ordinary skill in the relevant art has generally been omitted for the sake of brevity. The accompanying drawings are used to help easily understand various technical features and it should be understood that the embodiments presented herein are not limited by the accompanying drawings. As such, the present disclosure should be construed to extend to any alterations, equivalents and substitutes in addition to those which are particularly set out in the accompanying drawings.

Recently, mobile terminals become realized as smart terminals configured to perform the functions related with production and consumption of contents after developing from past communication functions such as multimedia players having combined functions.

Such smart terminals have been expanded diverse objects as well as conventional mobile terminals so as to perform diverse functions for objects independently or via interworking between smart terminals or objects.

Especially, such a smart terminal is extensively applicable even to an object which is wearable on a user, in other words, a wearable device.

Examples of the wearable device may include from a smartwatch, a smart glass and a head mounted display (HMD) even to indispensable goods which users have to wear such as clothes and shoes.

Shoes as a wearable device, in other words, smart shoes are configured to perform a function of informing a user via a smart terminal such as a mobile terminal or autonomously by analyzing information about the user's or wearer's activities.

More specifically, a smart shoe may perform functions of detecting, sensing or recording the activity time, activity distance, and activity locus while the wearer or user is wearing the smart shoe.

A motion sensor is used in measuring the location of the smart shoe on a 2-dimensional or 3-dimensional space such as the wearer's activity distance or locus.

Such a motion sensor is able to figure out not only an approximate location by using Global Positioning System (GPS) but also a specific location by using an acceleration sensor and a gyro sensor.

Moreover, the motion sensor may measure the speed of the smart shoes and calculate whether the wearer is walking or a standard of walk units.

In this instance, the motion sensor has to maintain a state of measuring the location of the smart shoes consistently, in other words, an electricity consuming state. Because of that, the smart shoes have a disadvantage of large battery consumption and an accompanying disadvantage in reducing the overall weight of the smart shoes.

In addition, when the wearer's activity locus is detected by using only a conventional motion sensor, the noise generated in the sensor could result in failure to identify the wearer's walks precisely such that a cumulative error might occur. In other words, the standard of the wearer's walk units is calculated wrongly enough to generate a problem in measuring the records.

FIG. 1 is a block diagram to describe a smart shoe module 200 in accordance with the present invention.

The smart shoe module 200 may include a wireless communication unit 310, an input unit 320, a sensing unit 340, an output unit 350, an interface unit 360, a memory 370, a controller 380 and a power supply unit 390. The elements shown in FIG. 1 are not necessarily required and the smart shoe module described in the specification may include more or less elements mentioned above.

More specifically, the wireless communication unit 310 of the above-noted elements may include one or more modules configured to facilitate wireless communication between the smart shoe module 200 and a wireless communication system, between the smart shoe module 200 and another mobile terminal or between the smart shoe module 200 and an external server. As another example, the wireless communication unit 310 may include one or more modules configured to connect the smart shoe module 200 with one or more networks.

Such the wireless communication unit 310 may include one or more of the short range communication, location information modules 311 and 312.

The short range communication module 311 may be connected with the smart shoe module 200 via Bluetooth and transceive data.

The location information module 312 is configured to measure or transmit location information about the smart shoe module 200 and it may include the repeated concept with a motion sensor 343 which will be described later.

The input unit 320 may include a user input unit 321 (e.g., a touch key and a mechanical key) configured to receive information from a user. The voice or image data collected from the input unit 320 may be analyzed and processed into a user's control command. The input unit 320 may be employed to receive an input of an on-off function configured to activate or inactivate the functions of the smart shoe module 200 and it may be omitted to save production cost or lightening smart shoes, if necessary.

The sensing unit 340 may include one or more sensors configured to sense one or more of peripheral information and user information. As one example, the sensing unit 340 may include one or more of a proximity sensor 341, an illumination sensor 342, a touch sensor, an acceleration sensor 344, a magnetic sensor, a G-sensor, a gyroscope sensor 345 (hereinafter, the gyro sensor), a motion sensor 343, a RGB sensor, an infrared sensor (hereinafter, the IR sensor), a finger scan sensor, an ultrasonic sensor, an optical sensor, a battery gauge, an environment sensor (e.g., a barometer, a hygrometer, a thermometer, a radioactive sensor, a heat sensor, a gas sensor) and a chemical sensor (e.g., an e-nose, a health-care sensor, a biometric sensor). Meanwhile, the smart shoe module 200 described herein is able to combine and use the information sensed by the two or more of the sensors.

Especially, the acceleration sensor 344 and the gyro sensor 345 which will be mentioned herein may be provided in the motion sensor 343.

The motion sensor 343 loaded in the smart shoe module 200 may mean the configuration for directly sensing the motion of the smart shoe module 200. The motion sensor 343 may include the acceleration sensor 344 and the gyro sensor 345. If necessary, it may include one of the two acceleration and gyro sensors 344 and 345.

The motion sensor 343 may sense the motion on a 2-dimensions or 3-dimensions of the smart shoe module 200 and location variation with respect to time.

The controller 380 may control the power supply unit 390 to supply the electric currents required by the motion sensor 343. The controller 380 may include physical parts of MCU (Micro Controller Unit) such as Central Processing Unit (CPU).

The motion sensor 343 and the controller 380 may be provided in the smart shoe module 200 or loaded in the smart shoes 100 as independent structures.

The pressure sensor 346 may be implemented by the smart shoe module 200. The pressure sensor 346 may be provided in the motion sensor in terms of its function. However, the motion sensor 343 in accordance with the present invention may include the acceleration sensor 344 and the gyro sensor 345. The pressure sensor 346 may be independently provided from the motion sensor 343.

The output unit 350 may be configured to generate the outputs related with sight, hearing or touch. The output unit 350 may include one or more of a display unit 351, an audio output unit 352, a haptic module 353 and an optical output unit 354.

The interface unit 360 may be employed as a passage to diverse external devices connected with the smart shoe module 200. Such the interface unit 360 may include one or more of an external charger port, a wired or wireless data port, a memory card port, a port for connecting a device including an identity module. The smart shoe module 200 may perform the proper control which is related with the connected external device, in response to the connection between the interface unit 360 and the external device.

The data for supporting the diverse functions of the smart shoe module 200 is stored in the memory 370. The data and commands for the operation of the controller implemented in the smart shoe module 200 may be stored in the memory 370.

The controller 380 may typically control the overall operation of the smart shoe module 200 as well as the operations related with the above-noted application programs. The controller 380 may process the signal, data and information input or output via the elements mentioned above or use the data and commands stored in the memory 370 so as to provide or process proper information or functions to the user.

The power supply unit 390 may be supplied the external power and the internal power under the control of the controller 380 and supply the electric power to each of the elements provided in the smart shoe module 200. Such the power supply unit 390 may include a battery and the battery may be an embedded or exchangeable type.

Some of the elements may be implemented via interworking so as to realize the operation and control of the smart shoe module 200 or a control method of the smart shoe module 200. The operation, control or control method of the smart shoe module 200 may be realized on the smart shoe module 200 based on at least one of the data and commands stored in the memory 370.

Figure 2:
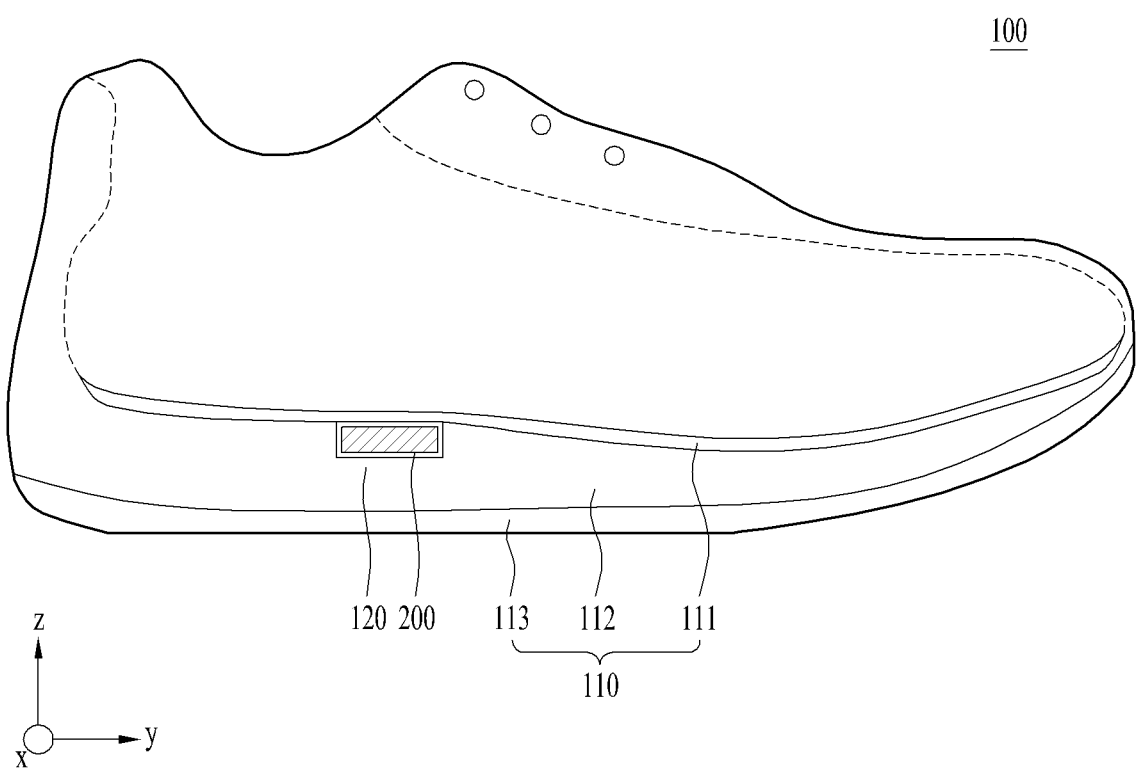
FIG. 2 is a sectional diagram of the smart shoes including the smart shoe module in accordance with the present invention along Y-Z.

FIG. 2 is a sectional diagram of the smart shoes 100 including the smart shoe module 200 in accordance with the present invention along Y-Z.

A shoe sole frame 110 means a direct and indirect area configured to contact with a sole of the wearer's foot. In other words, the shoe sole frame 110 may means the frame of the area provided between the sole of the wearer's foot and the floor. The shoe sole frame 110 may include an insole 111 provided to directly contact with the sole of the wearer's foot; an outsole 113 provided in a bottom of the smart shoe module 200 and configured to directly contact with the outside, in other words, the floor or ground; and a midsole 112 provided between the insole 111 and the outsole 113 and forming a preset volume.

The insole 111 may be a conventional shoe sole. If necessary, the insole 111 and the midsole 112 may be integrally formed with each other, without dividing them or coupled to each other by an auxiliary member or adhesive material.

The smart shoe module 200 may be provided in the shoe sole frame 110. The smart shoe module 200 may encode or data presence of an activated pressure when the shoe sole frame 110 is touching the ground by the wearer's walking or running.

Figure 3:
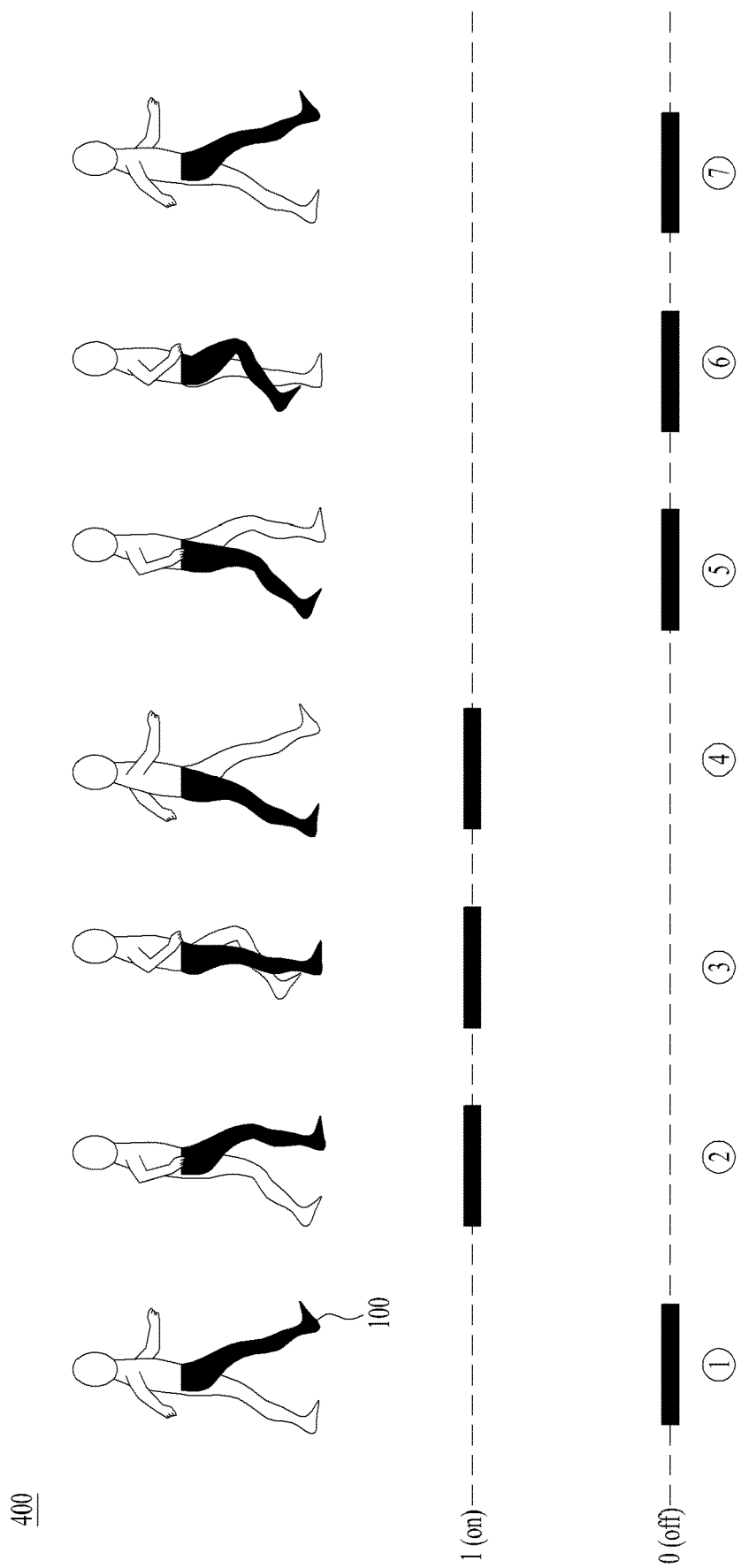
FIG. 3 is diagram a time-sequentially illustrating a smart-shoe wearer who is walking and response to a signal corresponding to the signal generated in response to the shape of the walking wearer.

FIG. 3 is diagram a time-sequentially illustrating the wearer 400 of the smart-shoe 200 who is walking and response to a signal corresponding to the signal generated in response to the shape of the walking wearer.

When the wearer 400 of the smart shoe module 200 takes a step on the ground, an on-signal may be generated in the smart shoe module 200. When the wearer 400 of the smart shoe module 200 takes the foot off the ground, an off-signal may be generated in the smart shoe module 200.

A specific pressure value or more is activated in a state of ② through ④ shown in FIG. 3 and a value of '1', in other words, the on-signal is generated in the smart shoe module 200. A value less than the specific pressure value is activated in a state of the other ① and ⑤ through ⑦ and a value of '0', in other words, the off-signal is generated in the smart shoe module 200.

More specifically, the wearer's body part of the smart shoe module 200 is put on the ground and a preset pressure is activated to the smart shoe module 200 provided between the wearer's body part and the ground, only to generate the on-signal.

The on-signal generated in the smart shoe module 200 may have a signal generation threshold pressure value.

When a pressure having the signal generation threshold pressure value or more is applied to the smart shoe module 200, the on-signal may be generated in the smart shoe module 200.

The signal generation threshold pressure value may be determined based on the material hardness and elasticity of the smart shoe module 200, the size of the smart shoe module 200 or a gap between a conductive member and a first circuit unit.

As one example, when the signal generation threshold pressure value is determined to be larger, the pressure threshold for generating the on-signal becomes higher. Only in a state of ② or ③, the value of '1', in other words, the on-signal may be generated in the smart shoe module 200. In a state of the other ① and ④ through ⑦, the value of '0', in other words, the off-signal may be generated in the smart shoe module 200.

Accordingly, the start and end of one step made by the wearer may be determined and when steps are repeated, a cycle of each step may be figured out.

In the embodiment shown in FIG. 3, ② may be analyzed as the start of one walking step and a position to be ① past ⑦ may be analyzed as the end of one walking step.

One cycle when the change from ② to ① is repeated is determined as one step so as to analyze a plurality of walking steps.

More specifically, when the position at which a speed value of the smart shoe module 200 gained from the unit of walks analyzed by the conventional motion sensor (343, see FIG. 1), in other words, the acceleration sensor (344, see FIG. 1) or the gyro sensor (345, see FIG. 1) is '0' (zero), several variables, in other words, noise may be activated to cause an error. However, such noise may be removed by using the on-off-signal of the smart shoe module 200 and the precise walk unit may be then distinguished.

The smart shoe module 200 may be implemented based on whether the pressure is activated in a direction to the shoe sole frame (110, see FIG. 2) from the sole of the wearer's foot, in other words, a downward direction. In this instance, the downward direction is not necessarily required and the pressure may be activated in a preset direction which is out of the downward direction by a preset angle. When a plurality of smart shoe modules 200 are provided, the pressure activated direction may be several directions.

The pressure direction may be determined based on the wearer's normal walk and force activation or it may be variable based on every wearer's different walk and force activation.

The threshold pressure value may be differently applied according to the wearer's physical and habitual factors such as the height, weight and shoe size. It is subordinate to the material and structure whether to switch on and off the smart shoe module 200 and the smart shoe module 200 having the fixed material and structure may have a preset threshold pressure value.

Figure 4:
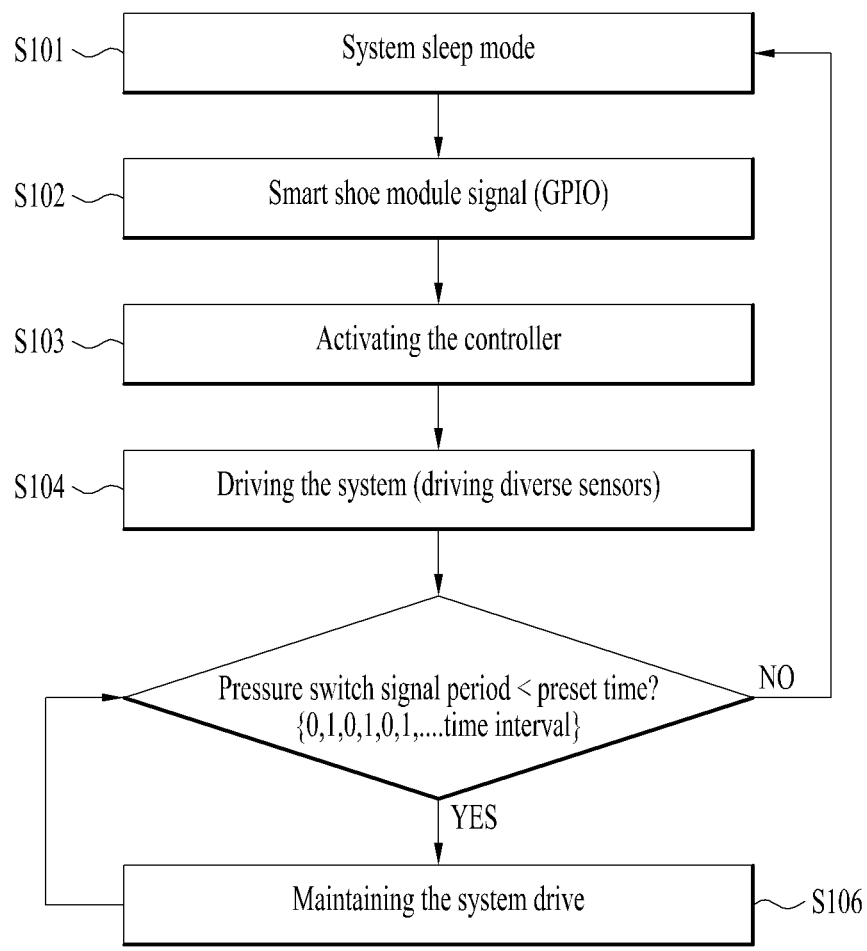
FIG. 4 is a flow chart illustrating the smart shoe module in accordance with the present invention.

FIG. 4 is a flow chart illustrating the smart shoe module 200 in accordance with the present invention.

The controller 380 may perform the current supply to and control of the motion sensor 343 based on the on or off signal of the smart shoe module 200.

When the off-signal is continuously generated in the smart shoe module 200 for a preset time period or more, it may be determined that the wearer is not wearing the smart shoe module 200 or walking.

Accordingly, the controller may inactivate the motion sensor 343 and implement a system sleep mode configured to minimize the electric power consumed by the smart shoe module 200 (S101).

When the on-signal is generated in the smart shoe module 200 during the system sleep mode, it may be analyzed that the wearer puts on the smart shoe module 200 and starts to walk (S102).

The electric current of the on-signal generated in the smart shoe module 200 during the system sleep mode may activate the controller 380 (S103). When the controller 380 is already activated, the step may be omitted.

The activated controller 380 may cancel the system sleep mode of the smart shoe module 200 and drive the system. The drive of the system may mean the drive of the various electronic components and sensors provided in the smart shoe module 200. Especially, the motion sensor 343 is activated and then it may be controlled to sense the motion of the smart shoe module 200 by using the acceleration sensor 344 and the gyro sensor 345. (S104).

The controller may compare the time interval between the on-signal generation and the off-signal generation in the smart shoe module in real time (S105).

When the time interval between the on-signal generation and the off-signal generation in the smart shoe module 200 is shorter than a preset time interval, in other words, an ON value of '1' is received in a preset time period, the drive of the smart shoe module 200 may be continuously maintained. Especially, the activation of the motion sensor 343 may be continuously maintained (S106).

In contrast, when the time interval between the on-signal generation and the off-signal generation in the smart shoe module 200 is longer than the preset time interval, in other words, an OFF value is continuously '0' for a preset time period or more, the controller 380 may inactivate the entire system of the smart shoe module 200, in other words, convert the current mode into the system sleep mode. Especially, the controller 380 may cut off the electric currents supplied to the motion sensor 343 and inactivate the motion sensor 343.

Figure 5:
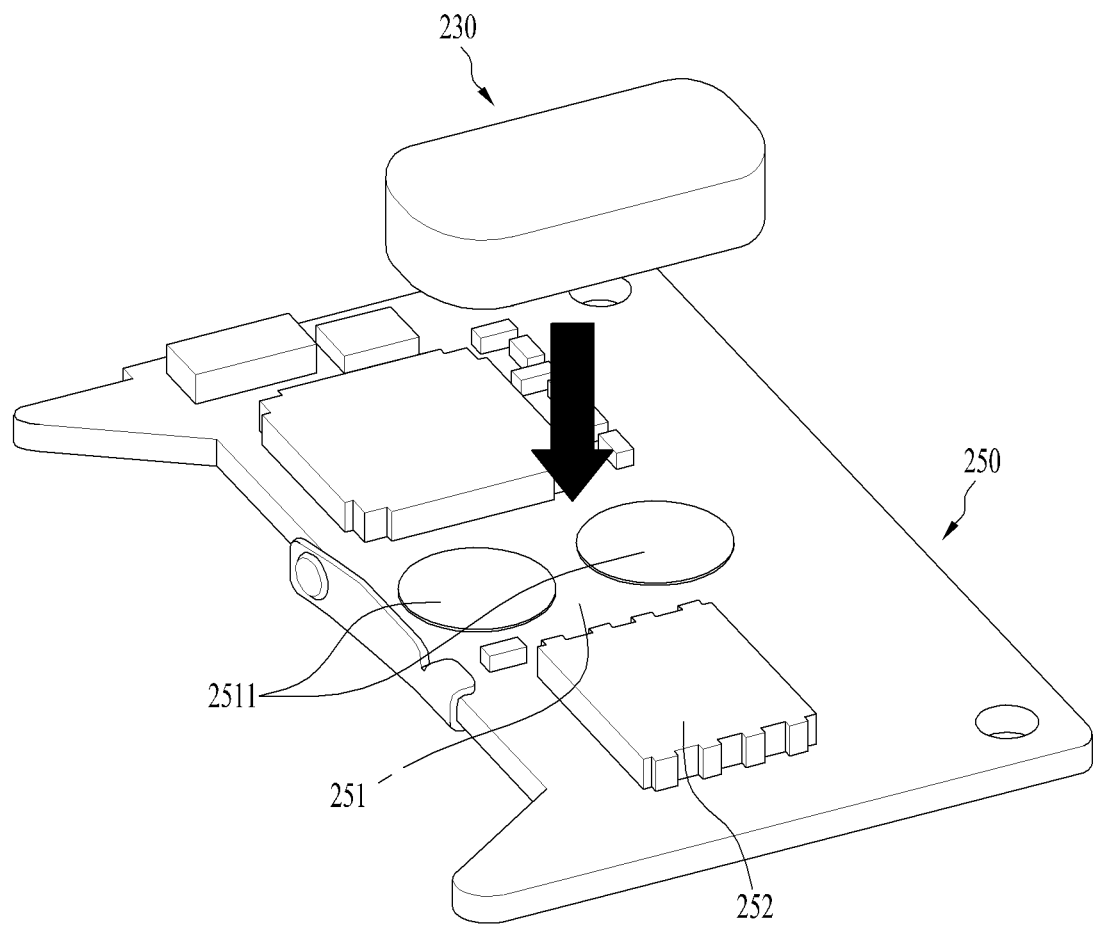
FIG. 5 is a diagram illustrating a conductive member and a first circuit unit in accordance with the present invention.

FIG. 5 is a diagram illustrating a conductive member 230 and a first circuit unit 251 in accordance with the present invention.

The pressure conductive member 230 may be operable in association with the first circuit unit 251. The first circuit unit 251 may be loaded in a circuit board 250, with a predetermined region exposed to the circuit board 250. FIG. 5 schematically illustrates a state before the conductive member 230 and the first circuit board 251 are coupled to each other for easy description. The conductive member 230 may be fixed in a state of spaced apart from the circuit board 250 by another auxiliary material or by contact.

When a pressure having a value less than a specific value is activated on the pressure smart shoe module 200, the conductive member 230 is electrically disconnected from the first circuit unit 251.

Before the first circuit unit 251 is connected with the pressure conductive member 230, the first circuit unit 251 may be kept as an open circuit, in other words, in an electrically open state. The first circuit unit 251 in such an electrically open state may be realized by two contact terminals 2511 which are distant from each other.

When a specific pressure value or more is activated on the pressure smart shoe module 200, the conductive member 230 may be electrically connected with the contact terminals 2511 of the first circuit unit 251.

The two distance contact terminals 2511 may be electrically connected with each other by the conductive member to make the first circuit unit 251 a closed circuit. When the first circuit unit 251 becomes the closed circuit, an electric current or signal may be generated.

The first circuit unit 251 may generate an electric current or signal by electrical contact.

The controller (380, see FIG. 1) may recognize presence of the electric current or signal generated in the first circuit unit 251 as the on-off-signal and control diverse following operations based on the on-off-signal.

It may be analyzed as one additional independent process that the controller (380, see FIG. 1) recognizes the on-off-signal based on the presence of the electric current or signal generated in the first circuit unit 251. However, it may mean one operation which is configured to be performed in one same circuit. In other words, the electric current generated in the first circuit unit 251 may electrically connect the controller (380, see FIG. 1) right away, to be recognized as the on-off-signal.

Figure 6:
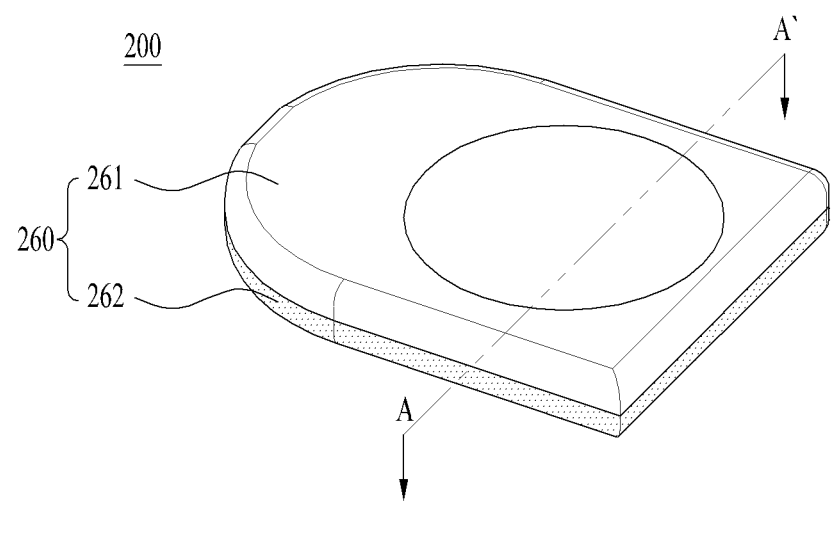
FIG. 6 is a diagram illustrating one embodiment of the smart shoe module.
Figure 6:
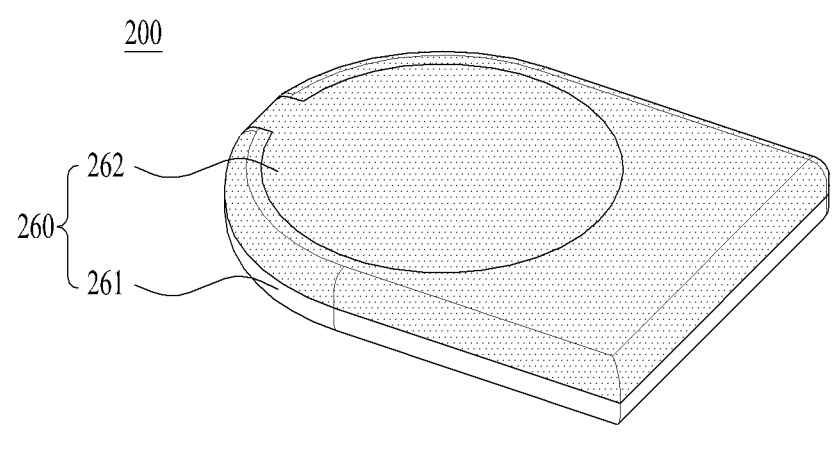

FIG. 6 is a diagram illustrating one embodiment of the smart shoe module 200.

FIG. 6 (*a*) is a front perspective view of the smart shoe module 200 and FIG. 6 (*b*) is a rear perspective view of the smart shoe module 200.

The smart shoe module 200 may include a housing 260 provided to define an exterior of the smart shoe module and the housing 260 may include an upper case 261 and a lower case 262. Alternatively, the upper case 261 and the lower case 262 may be integrally formed with each other as uni-body. In the present invention, it is suggested that the upper 261 and the lower case 262 may be formed as independent bodies, respectively, and the cases may be coupled to each other.

The terms of 'upper and lower' of the upper and lower cases 261 and 262 are limited for easy and convenient description and the upper and lower cases may be reversed within its scope as defined in the appended claims. Alternatively, a first case and a second case may be provided and coupled to each other, instead of the upper case 261 and the lower case 262, or three or more cases may be provided and coupled to each other.

Figure 7:
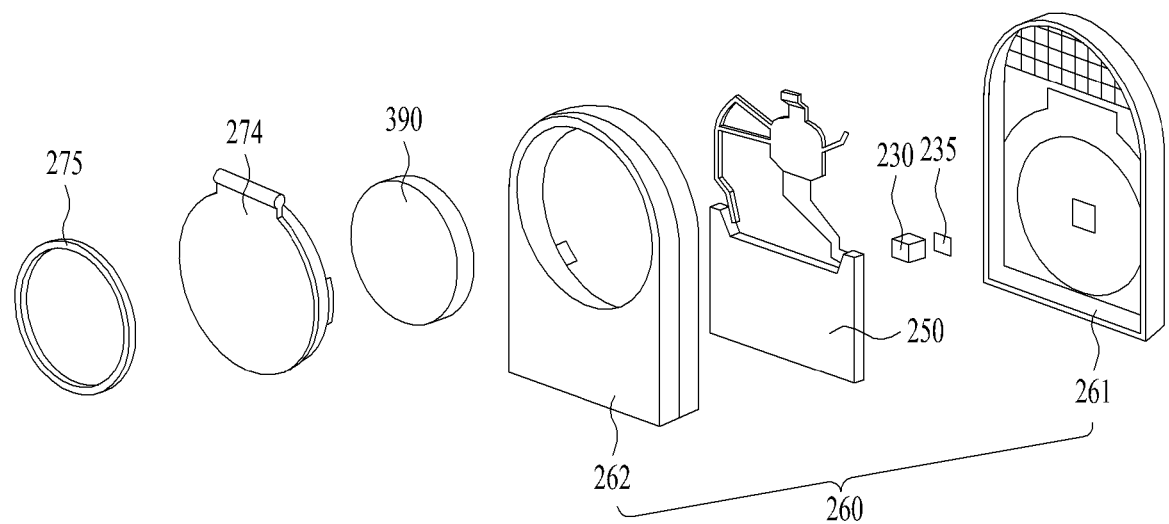
FIG. 7 is a diagram another embodiment of the smart shoe module.

FIG. 7 is a diagram another embodiment of the smart shoe module 200.

The smart shoe module 200 may mean the structural unit in which the components configured to perform the function of the pressure sensor (346, see FIG. 1) are loaded and it may physically include the overall structure loaded in the housing 260.

Predetermined components including the circuit board 250 may be loaded in the housing 260. The upper case 261 provided in a front surface of the housing 260 and the lower case 262 may be coupled to each other.

The power supply unit 390 may be loaded in the housing 260 and configured to supply the electric power to the power supply controller 380.

For smooth exchange of the power supply unit 390, a battery cover 274 may be further provided and the battery cover 274 may be coupled to the lower case 262.

A waterproof ring 275 may be provided to seal a gap formed between the battery cover 274 and the lower case 262 so as to prevent a waterproof problem.

Figure 8:
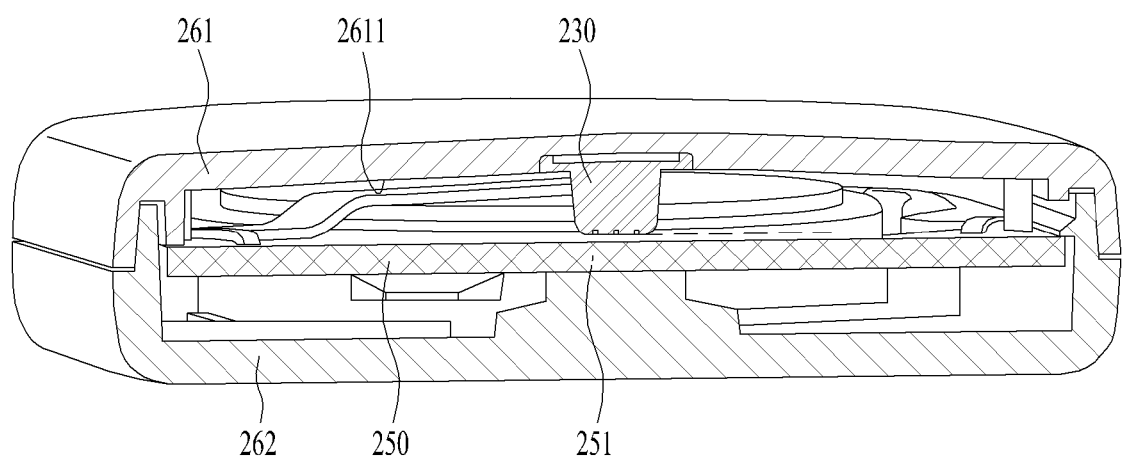
FIG. 8 is a sectional diagram along A-A of FIG. 6.

FIG. 8 is a sectional diagram along A-A' of FIG. 6.

The upper case 261 may define the upper exterior of the smart shoe module 200 and it may be elastically movable by a specific pressure value or more which activates in a first direction. The first direction may mean the direction from the wearer's foot to the ground, in other words, from the upper case 261 to the lower case 262.

The specific pressure value or more may mean the signal generation threshold pressure value mentioned above.

The upper case 261 may have a thin flat shape to transfer the pressure to the conductive member 230 from the sole of the wearer's foot efficiently, in direct contact with the conductive member 230. An outer surface of the upper case 261 is convex to transfer the pressure from the wearer's foot to the shoe sole and then the upper case 261 efficiently. If necessary, the upper case 261 may include a flexible material to transfer the pressure to the conductive member 230. As one example, the upper case 261 may be formed of silicon.

The lower case 262 may be coupled to a lower end of the upper case 261 and configured to define a lower exterior of the smart shoe module 200.

The first circuit unit 251 may be loaded in the housing 260 formed by the upper and lower cases 261 and 262. Especially, the first circuit unit 251 may be fixed to the lower case 262.

A predetermined area of the first circuit unit 251 is exposed to one surface of the circuit board 250 to contact or become in contact with the conductive member 230 which will be described later.

The first circuit unit 251 may be provided as a combined form configured of a film and a metal electrode or a film and a conductive polymer. Alternatively, the first circuit unit 251 may be configured of a film and CNT or a film and graphene.

As another example, the first circuit unit 251 may be configured of an injection molding and Mold Interconnect Devices (MID).

The circuit board 250 may have the first circuit unit 251 loaded thereon. The circuit board 250 may further have a second circuit unit loaded thereon to drive the motion sensor 343. The circuit board 250 may also have the controller (380, see FIG. 1) loaded thereon. However, it is not necessary that the smart shoe module 200 should include the motion sensor 343, the second circuit board and the controller 380. The smart shoes 100 may include a motion sensor 343, a second circuit unit or a controller (380, see FIG. 1) which is provided as auxiliary independent element or it may include at least one of those elements.

The conductive member 230 may be configured to generate an electrical signal in the first circuit unit 251.

The conductive member 230 may be loaded in the housing 260 defined by the upper case 261 and the lower case 262, especially, in the upper case 261.

The conductive member 230 may be provided in the upper case 261 and form a first gap together with the first circuit unit 251. The conductive member 230 may be elastically movable by a specific pressure value or more which is applied to the upper case 261 in a first direction so as to contact with the first circuit unit 251 and generate a signal.

More specifically, the conductive member 230 may perform the function of the pressure sensor (356, see FIG. 1) according to the presence of the specific pressure value or more which is activated on the upper case 261 by contacting with the first circuit unit 251. When the specific pressure value or more is activated on the smart shoe module 200, an electrical signal is generated in the first circuit unit 251.

The conductive member 230 may be employed to electrically connect the first circuit unit 251 when contacting with the first circuit unit 251. The conductive member 230 may include a conductive material which facilitates electric current flow. Accordingly, examples of the conductive material may include conductive silicon, a metal gasket, a metal plate or metal deposition, conductive polymer, CNT and graphene.

As another example, the conductive member may be provided as a combined form configured of an injection molding and MID (Mold Interconnect Devices).

For easy description sake, a state where no pressure is activated on the smart shoe module 200 is referred to as 'a neutral state' and a state where the specific pressure value or more is activated on the smart shoe module 200 is referred to as 'a compression state'

In the neutral state, the conductive member and the first circuit unit 251 may form a first gap (G1). The first gap (G1) may have a specific value of more than 0 mm.

The first gap (G1) is maintained in the neutral state. The conductive member 230 and the first circuit board 251 may be in contact with each other by the elastic motion of the upper case 261 in the compression state.

When manufacturing the smart shoe module 200, the first gap (G1) could be variable by a manufacture tolerance of the upper and lower cases 261 and 262, a manufacturing tolerance and a coupling tolerance of the conductive member 230 and the circuit board 250 including the first circuit unit 251, a coupling tolerance of the conductive member 230 and the upper case 261 and a coupling tolerance of the upper and lower cases 261 and 262.

Unless the first gap (G1) has a constant value, a threshold pressure value of the signal generation may be variable to form no precise line between the on-signal and the off-signal.

If real walk is recognized as no walk generation or no walk generation is recognized as real walk by an error in separating the on-signal from the off-signal, cumulative errors occur in the wearer's walk pattern analysis to bring in a problem.

Accordingly, reliability is required to maintain the first gap (G1) in the neutral state, in other words, to generate no on-signal by the contact between the conductive member 230 and the first circuit unit 251.

The upper case 261 and the lower case 262 may be coupled to each other by coupling a coupling hole 263 to a coupling projection 264.

The coupling hole 263 and the coupling projection 264 may be forcibly fitted to each other so as to prevent the upper and lower cases 261 and 262 from becoming open unintendedly.

The coupling hole 263 may be provided in the upper or lower case 261 or 262 and the coupling projection 264 may be provided in the other.

A lateral surface of the coupling hole 263 and a lateral surface of the coupling projection 264 may contact with each other to show an effect of forcibly fitting.

The coupling hole 263 and the coupling projection 264 may form a second gap (G2) in a longitudinal direction in which they are coupled to each other. The second gap (G2) may be configured to prevent the width of the first gap (G1) from being variable by a tolerance between the coupling hole 263 and the coupling projection 264.

For a similar purpose, a third gap (G3) may be formed in an outer line of the coupled upper and lower cases 261 and 262.

A support rib 265 may be downwardly projected from an inner surface of the upper case 261 to support the circuit board 250 including the first circuit unit 251.

To minimize the tolerance generated in the first gap (G1) by the play when the first circuit unit 251 is loaded in the lower case 262, the support rib 265 may be employed to support and stop the circuit board 250 including the first circuit unit 251 from moving.

A hook portion 266 may be projected from an inner surface of the lower case 262 and configured to fix the circuit board 250 including the first circuit unit 251.

The conductive member 230 may be coupled to an inner surface 2611 of the upper case 261. The coupling may be performed by using an adhesive tape 235 (FIG. 7) or a double-injection molding at the same time when or after the upper case 261 is fabricated.

Figure 9:
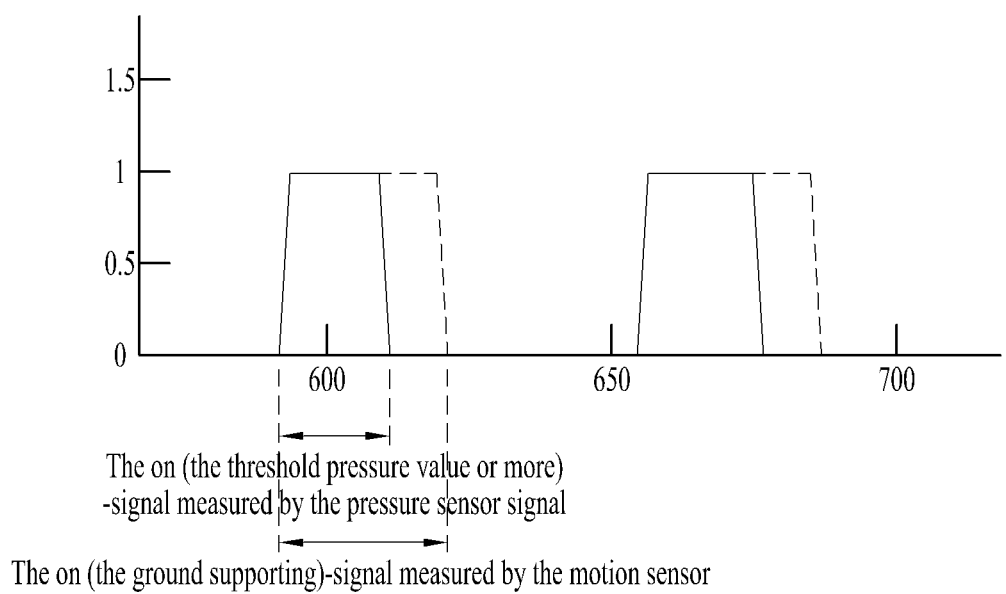
FIG. 9 is a diagram illustrating one embodiment of the time variance of the on-signal measured by the motion sensor of the smart shoes.

FIG. 9 is a diagram illustrating one embodiment of the time variance of the on-signal measured by the motion sensor 343 of the smart shoes 100.

The motion sensor 343 mentioned above is able to recognize the location of the smart shoes 100 on a 3-dimensional location by using the acceleration sensor 344 and the gyro sensor 345 in real time.

Accordingly, the controller 380 may check and analyze whether the smart shoes 100 are in an on-signal state where the smart shoes are supporting the ground, in other words, in a state of '1' value or in an off-signal state where they are off from the ground, in other words, a state of '0' value.

Meanwhile, the pressure sensor 346 mentioned above may analyze the on-signal state where it is estimated that the smart shoes 100 are on the ground or the off-signal state where it is estimated that they are off from the ground based on whether the pressure value is the signal generation threshold pressure value or more.

In this instance, when the pressure sensor 346 determines whether the on-signal or the off-signal is generated, an error could be generated by the manufacturing or coupling tolerance of the smart shoe module 200 mentioned above.

Accordingly, it is necessary to calibrate the state of the on or off-signal measured and analyzed by the pressure sensor 346 into the state of the on or off-signal measured and analyzed by the motion sensor 343.

Figure 10:
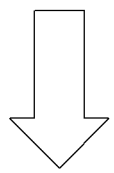
FIG. 10 is a diagram illustrating an algorithm configured to calibrate a smart-shoe-on-signal time value measured by a pressure sensor into a smart-shoe-on-signal time measured by a motion sensor.
Figure 11:
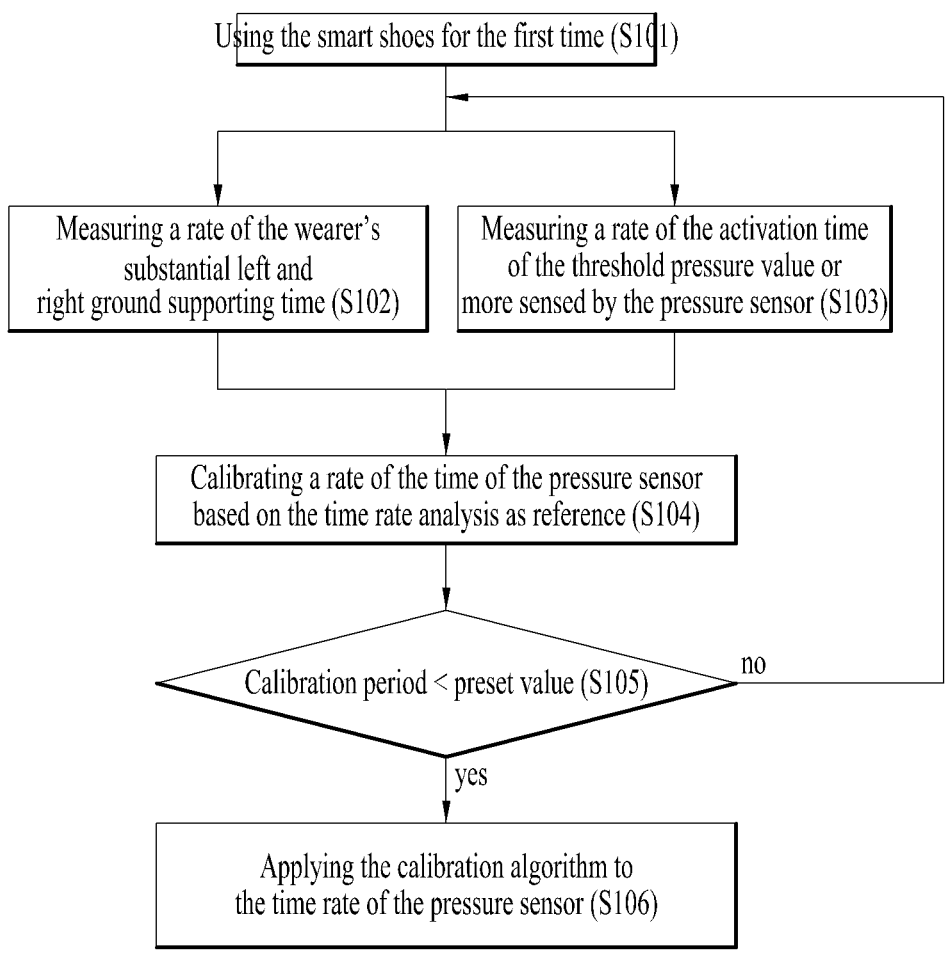
FIG. 11 is a flow chart to calibrate the smart-shoe-on-signal time value measured by the pressure sensor into the smart-shoe-on-signal time measured by the motion sensor.

FIGS. 10 11 are diagrams illustrating an algorithm and a flow chart configured to calibrate a smart-shoe-on-signal time value measured by the pressure sensor 346 into a smart-shoe-on-signal time measured by the motion sensor 343.

The smart shoe module 200 may be provided in each of the left and right smart shoes 100 and configured to analyze the wearer's walk pattern.

The smart shoe module 200 provided in the left smart shoe 100 may be defined as the left smart shoe module 200-1 and the smart shoe module 200 provided in the right smart shoe 100 may be defined as the right smart shoe module 200-2. The units which are organically measured and analyzed by the left smart shoe module 200-1 and the right smart shoe module 200-2 may be defined as the smart shoe module system 2001.

More specifically, the measured or analyzed value of the left smart shoe module 200-1 or the right smart shoe module 200-2 may be transmitted to the other one. Alternatively, an auxiliary terminal may be provided with the measured value and the analyzed values of the two smart shoe modules and configured to calibrate the values.

In the former case, the left smart shoe module 200-1 and the right smart shoe module 200-2 may form the smart shoe module system 2001. In the latter case, the left smart shoe module 200-1, the right smart shoe module 200-2 and the auxiliary terminal may form the smart shoe module system 2001.

An error between the pressure sensor 346 and the motion sensor 343 shown in FIG. 9 may be expanded even to a problem of an on-signal duration time of the left and right smart shoes 100.

The left smart shoe 100 and the right smart shoe 100 may be different from each other in the support time with respect to the ground according to the wearer's walk pattern, in other words, the time while the specific pressure value or more is applied or the rate of the time. Accordingly, such difference or deviation might bring about incorrect results in analyzing the wearer's walk pattern and it may be then necessary to calibrate the difference or deviation.

Not only the manufacturing tolerances of the left and right smart shoe modules 200 mentioned above but also the combined factors including the deviation caused by the weight unbalance between the wearer's left and right weights might cause left and right deviation about the analysis of the support time while the left and right smart shoe modules are supporting the ground.

It may be necessary to calibrate the deviation of the support times between the left and right smart shoes 100 measured by the pressure sensor 246.

The compensation may be realized by analyzing the support times of the motion sensors 343 provided in the left and right smart shoes 100, respectively, with respect to the ground.

As mentioned above, the motion sensor 343 may measure the locations of the left and right smart shoes 100 on a 3-dimensional space by using the acceleration sensor 344 and the gyro sensor 345 in real time.

The controller 380 may control the motion sensor 343 to analyze a start point and an end point of the smart shoes' 100 substantially supporting the ground.

The rate of the time spent in each of the left and right smart shoes 100 supporting the ground, which is measured by the motion sensor 343, may be set as the reference. The deviation between the reference and the rate of the on-signal time of the left and right smart shoes 100 sensed by the pressure sensor 346 may calibrated.

As one example, when the smart shoes 100 are used for the first time, the calibration algorithm may be automatically implemented (S101).

The controller 380 may analyze the rate of the ground supporting time via the 3D motion of the left and right smart shoes 100 measured by the motion sensor 343 including the acceleration sensor 344 and the gyro sensor 345 (S102). The controller 380 may analyze the rate of the time spent while the threshold pressure value or more is activated on the left and right smart shoes 100, which is measured by the pressure sensor 346 (S103).

The measurement and the analysis of the former (S102) and the measurement and the analysis of the latter (S103) may be performed simultaneously or alternately.

As one example, the rate of the ground supporting time rate measured and analyzed by the motion sensor 343 is 0.8:1.2 and the rate of the time when the signal generation threshold pressure value or more measured and analyzed by the pressure sensor 346 is activated is 0.9:1.1.

In this instance, the controller 380 may apply the calibration algorithm configured to multiply the value measured by the pressure sensor 346 of the left smart shoe 100 by 0.8/0.9 and the value measured by the pressure sensor 346 of the right smart shoe 100 by 1.2/1.1 (S104 and S106).

At this time, to minimize the power consumption, the controller 380 needs to drive the motion sensor 343 only in an early calibration step of the pressure sensor 346 and inactivate the motion sensor 343 as long as no additional needs occur.

More specifically, when performing the calibration, the controller 380 may temporarily activate the inactivated motion sensor 343.

The controller 380 may perform the calibration according to the interval the user sets up or a preset interval automatically (S105).

In the smart shoe module 200 in the compression state, the conductive member 230 and the first circuit unit 251 may be physically in contact with each other. In the smart shoe module 200 in the neutral state, the conductive member 230 and the first circuit unit 251 may be physically spaced apart or keep the contact according to the embodiments.

If necessary, the conductive member 230 and the first circuit unit 251 may physically contact with each other and the conductive member 230 may be spaced a preset distance apart from an inner surface of the upper case 261.

Hereinafter, diverse embodiments which may occur according to the material and shape of the conductive member 230 will be described.

First Embodiment

Figure 12:
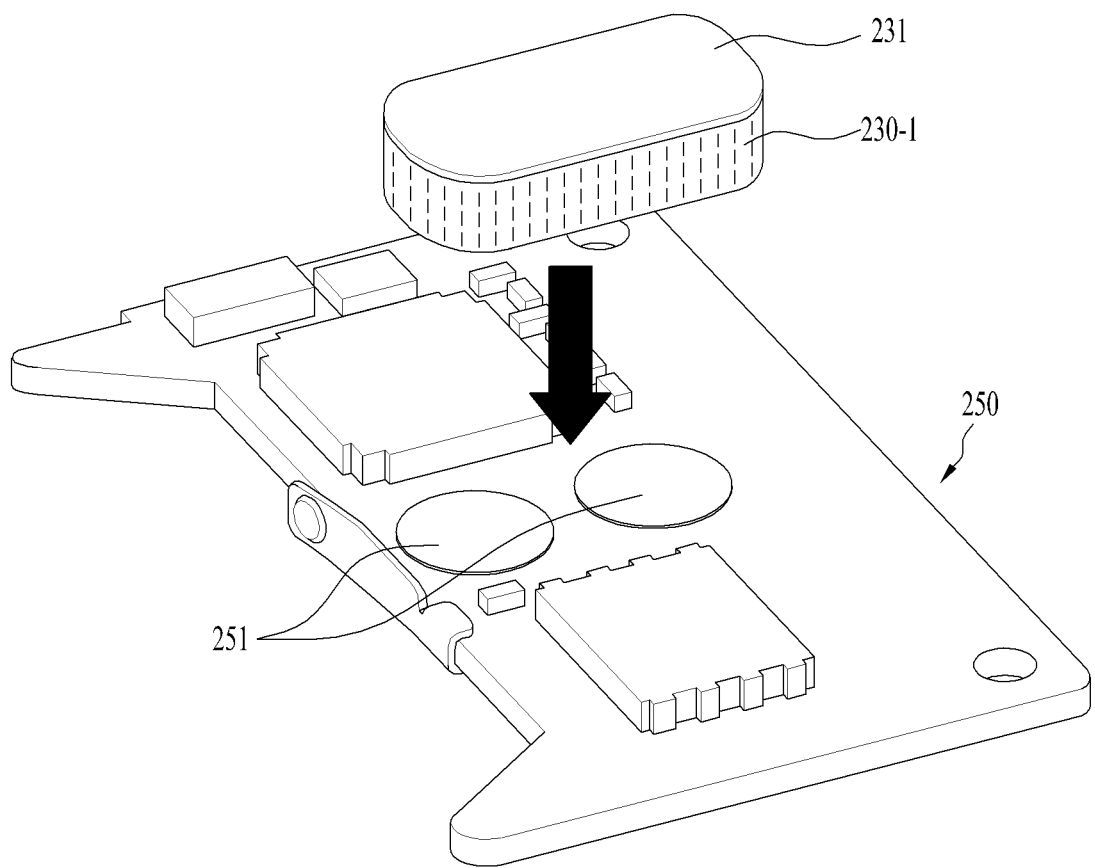
FIG. 12 is a diagram partially illustrating the smart shoe module when the conductive member is a variable resistance element.

FIG. 12 is a diagram partially illustrating the smart shoe module 200 when the conductive member 230 is a variable resistance element 230-1.

The conductive member 230 may include a variable resistance element 230-1. The variable resistance element 230-1 may mean a material of which resistance decreases according to the load applied thereto.

In the smart shoe module 200 in the neutral state, the variable resistance element 230-1 may have a preset interval with respect to the first circuit unit 251 or be in contact with the first circuit board 251. In the latter case, one surface of the variable resistance element 230-1 may contact with the upper case 261 and the other surface may contact with the first circuit board 251.

Alternatively, the variable resistance element 230-1 may be fixed to the circuit board 250, in contact with the first circuit unit 251, and it may be spaced a preset distance apart from the inner surface 2611 of the upper case 261.

In the smart shoe module 200 in the compression state, the resistance of the variable resistance element 230-1 may decrease to generate a signal in the first circuit unit 251.

The variable resistance element 230-1 may have a variable resistance according to a pressure degree even in a state of contacting with the first circuit unit 251. Accordingly, it is necessary that the controller 380 should perform calculation to recognize the on-signal and the off-signal of the smart shoe module 200 mentioned above based on a point at which the resistance of the variable resistance element 230-1 is a specific value or less, not based on the physical contact between the variable resistance element 230-1 and the first circuit unit 251.

In this instance, the resistance of the variable resistance element 230-1 is changed into a low resistance with respect to the compression direction. When the smart shoe module 200 is compressed vertically, the first circuit unit 251 might fail to form a closed circuit and secure reliability for the signal generation.

Accordingly, to calibrate such the defect, a conductive layer 231 may be further provided to cover at least predetermined area of an upper surface of the variable resistance element 230-1.

Electric currents in the vertical direction of the variable resistance element 230-1 may flow along the horizontal conductive layer and form the first circuit unit 251 as the closed circuit.

Second Embodiment

The conductive member 230 may be a piezo element 230-2.

The piezo element 230-2 may mean the element, which generates electric currents or voltages according to the pressure applied thereto or physically moves when the currents and voltages flow thereto.

In the smart shoe module 200 in the neutral state, the piezo element 230-2 may have a preset interval with respect to the first circuit unit 251 or be in contact with the first circuit board 251. In the latter case, one surface of the piezo element 230-2 may contact with the upper case 261 and the other surface may contact with the first circuit board 251.

Alternatively, the piezo element 230-2 may be fixed to the circuit board 250, in contact with the first circuit unit 251, and it may be spaced a preset distance apart from the inner surface 2611 of the upper case 261.

When the piezo element 230-2 of the smart shoe module 200 in the compression state is compressed, electric currents or voltages may occur. At this time, the compression degree tends to be proportional to the generated electric currents or voltages.

The electric current or voltage generated in the piezo element 230-2 may be converted into an electrical signal by using the first circuit unit 251. The controller 380 may measure the pressure degree based on the current or voltage of the signal generated in the first circuit unit 251 or determine whether a specific pressure value or more is applied to the smart shoe module 200.

The generated voltage of the piezo element 230-2 may be variable according to the compression degree even when contacting with the first circuit unit 251. Accordingly, it is necessary that the controller 380 should perform calculation to recognize the on-signal and the off-signal of the smart shoe module 200 mentioned above based on a point at which the electric current or voltage generated by the piezo element 230-2 is a specific value or more, not based on the physical contact between the piezo element 230-2 and the first circuit unit 251.

Figure 13:
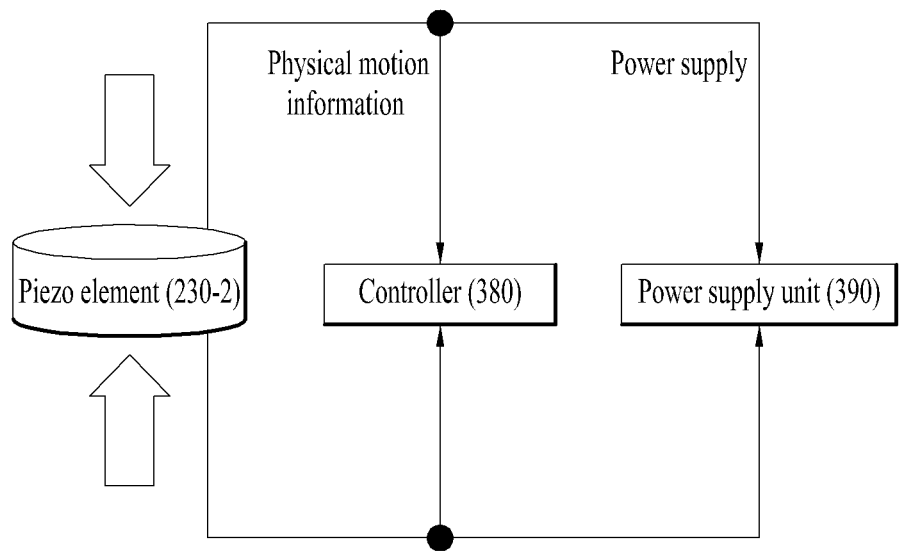
FIG. 13 is a block diagram illustrating the smart shoe module when the conductive member is a piezo element.

FIG. 13 is a block diagram illustrating the smart shoe module 200 when the conductive member 230 is the piezo element 230-2.

The piezo element 230-2 may generate the electric current or voltage according to the pressure applied thereto.

The controller 380 may calculate the user's momentum based on the electric current or voltage of the signal generated in the first circuit unit 251 by the piezo element 230-2.

More specifically, the piezo element 230-2 may not only determine whether the signal is the on or off-signal but also continuously provide the size of the current or voltage generated by the pressure to the controller 380 such that the controller 380 can use it in calculating the momentum.

When the conductive member 230 is the piezo element 230-2, the piezo element 230 may be employed to supply the energy used in accumulating the current or voltage.

The currents or voltages generated by the piezo element 230-2 may be used in the accumulation of the power for the power supply unit 390 configured to supply the electric power to the smart shoe module 200. In this instance, the use life span of the power supply unit 390 may be expanded semi-permanently or permanently.

Figure 14:
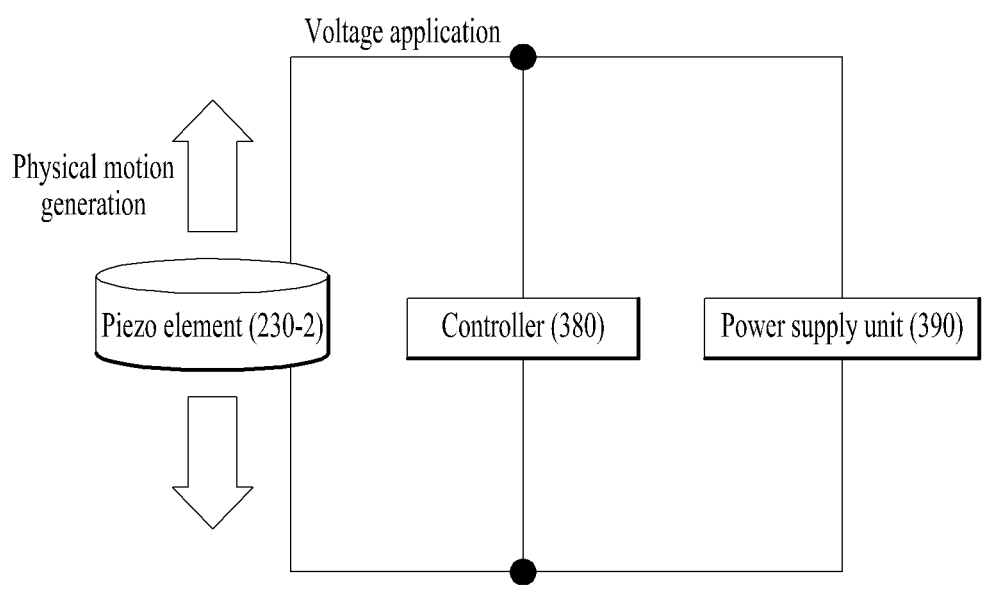
FIG. 14 is a block diagram illustrating the smart shoe module when the conductive member is the piezo element.

FIG. 14 is a block diagram illustrating the smart shoe module 200 when the conductive member 230 is the piezo element 230-2.

In contrast, the piezo element 230-2 may be employed to provide a physical motion to the smart shoe module 200 in response to the voltage of the controller 380.

The controller 380 may control the power supply unit 390 to apply a corresponding voltage to a preset control signal to the piezo element 230-2. The piezo element 380 may physically move in response to the applied voltage. As one embodiment, the physical motion of the piezo element 230-2 may be used as vibration for an alarm function.

In other words, the piezo element 230-2 provided as the conductive member 230 may be employed to perform the function of the pressure sensor (364, see FIG. 1) configured to figure out the user's motion and to give an alarm to the user by physically moving the smart shoe module 200.

FIGS. 15 through 18 are diagrams sequentially illustrating the embodiments which provide the user with the alarm by using the piezo element 230-2.

A preset control signal may make at least one of the applied voltage size, the voltage application frequency and the voltage application period to be variable.

As the applied voltage becomes larger, the phase of the piezo element's physical motion may be varied. The voltage application frequency and period may affect the diversification of the patterns which are recognizable by the user.

The smart shoe module 200 may be provided in each of the left and right smart shoes 100.

The smart shoe module 200 provided in the left smart shoe 100 may be defined as the left smart shoe module 200-1 and the smart shoe module 200 provided in the right smart shoe 100 may be defined as the right smart shoe module 200-2. The units which are organically operated in the left smart shoe module 200-1 and the right smart shoe module 200-2 may be defined as the smart shoe module system 2001.

More specifically, the controller 380 provided in the left smart shoe module 200-1 or the right smart shoe module 200-2 may control not only the smart shoe module in which it is provided but also the other one or the controllers 380 may control the corresponding smart shoe modules, respectively, and share information with each other to organically control them.

Alternatively, an auxiliary terminal may be provided with the measured value and the analyzed values of the two smart shoe modules and configured to calibrate the values.

In the former case, the left smart shoe module 200-1 and the right smart shoe module 200-2 may form the smart shoe module system 2001. In the latter case, the left smart shoe module 200-1, the right smart shoe module 200-2 and the auxiliary terminal may form the smart shoe module system 2001.

The piezo element 230-2 may be provided in each of the left and right smart shoe modules 200-1 and 200-2.

The preset control signal may be a first control signal configured to apply a voltage to one of the piezo elements 230-2. In other words, the first control signal may be the signal configured to generate vibration only in one of the smart shoe modules 200.

The preset control signal may be a second control signal configured to apply a voltage to both of the piezo elements. In other words, the second control signal may be a signal configured to generate vibration in both of the smart shoe modules 200.

The preset control signal may be a third control signal configured to apply a voltage to the piezo elements alternately. In other words, the third control signal may be a signal configured to generate vibration in the smart shoe modules 200 alternately.

Accordingly, the controller 380 may transfer diverse signals to the wearer by the combination of the vibration via the applied voltage size, frequency and period and the division of the left and right smart shoe modules 200.

As one example, the vibration strength may be varied according to the applied voltage size only to vary the importance of the alarms. The vibration generated only in one of the left and right smart shoe modules 200 may mean a traveling direction. The vibration generated in both of the left and right smart shoe modules 200 may mean the alarm to warn the wearer to stop. The vibration generated in the left and right smart shoe modules 200 alternately may mean the alarm to recommend the user to reverse the smart shoes.

Figure 15:
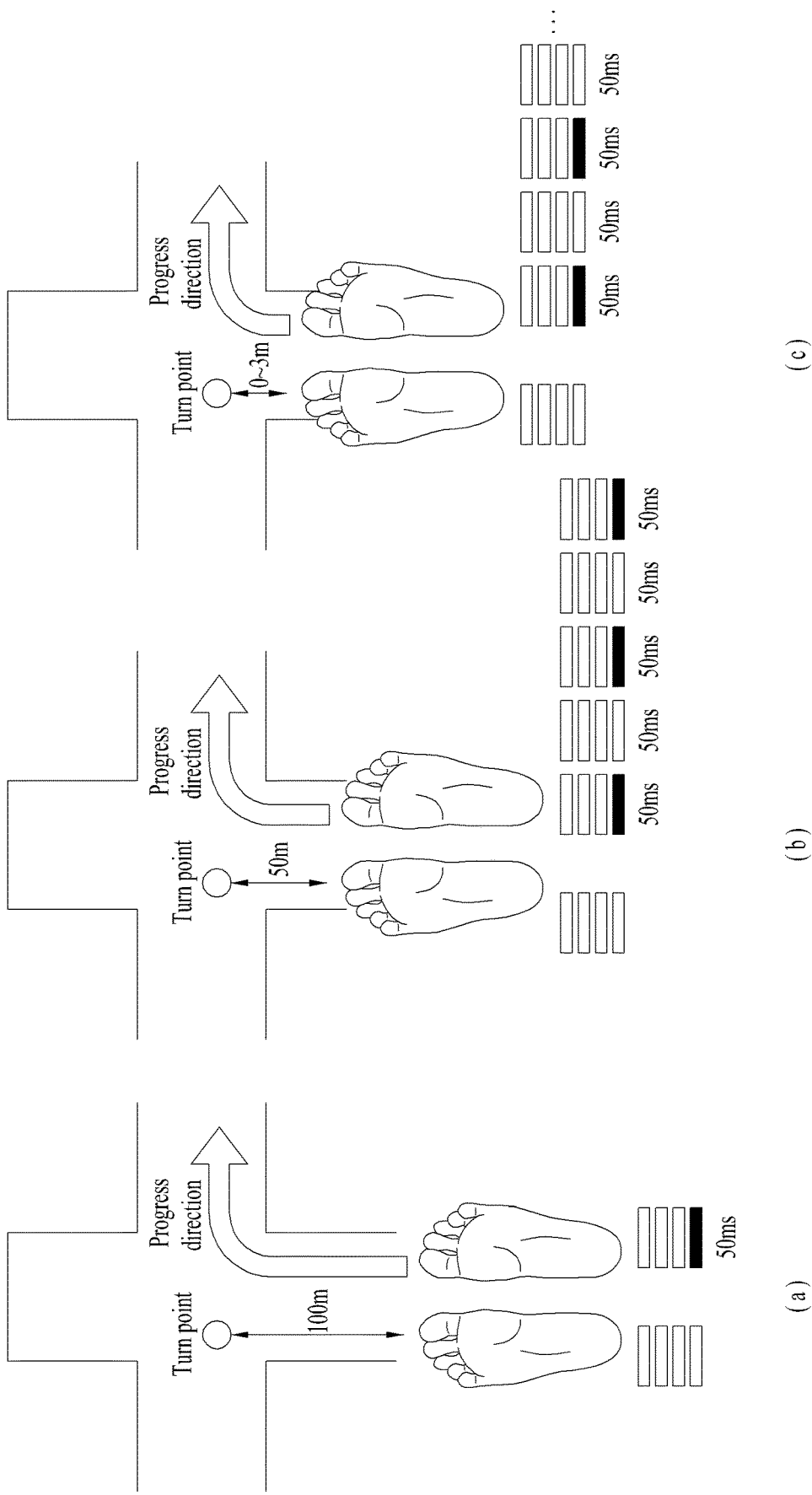
FIG. 15 is a diagram illustrating one embodiment of a piezo element vibration control signal configured to guide rotation.

FIG. 15 is a diagram illustrating one embodiment of the piezo element 230-2 vibration control signal configured to guide rotation.

The controller 380 may generate vibration in the smart shoe module which needs rotation. In other words, when right turn is needed, the controller 380 may generate vibration in the smart shoe module. In other words, when right turn is needed, vibration may be generated in the right smart shoe module 200-2. When left turn is needed, vibration may be generated in the left smart shoe module 200-1. Accordingly, the wearer is able to recognize the vibration as the alarm requiring turn.

If necessary, a vibration pattern may be varied as coming near to a turn requiring point so as to notice the wearer that the turn requiring point is coming closer to the turn requiring point. As one example, one vibration is generated 100 m away from the turn requiring point (see FIG. 15 (a)) and three vibrations are generated 50 m away (see FIG. 15 (b)). Constant vibrations are generated 3 m away from the turn requiring point until the required turn is made (see FIG. 15 (c)).

The number of black squares may mean proportion to the strength of vibration or the unit of 'ms' or 'sec' may mean the vibration, which will be applied even to FIGS. 13 through 15 equally.

The turn point may be acquired from the coordinate information preset in the memory based on a point of arrival which is set by the user or automatically or the coordinates information transmitted from a server.

As mentioned above, the location information module may measure and transmit location information about the smart shoe module 200 to the controller 380 such that the controller 380 can calculate a distance between the location information about the smart shoe module 200 and the turn point.

Such an algorithm may be equally applied even to FIGS. 16 through 18 which will be described later.

Figure 16:
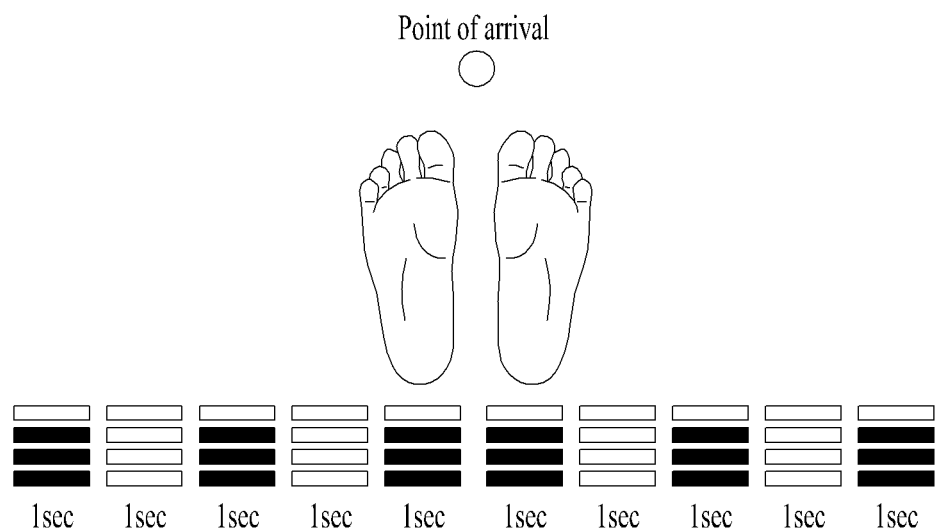
FIG. 16 is a diagram illustrating one embodiment of a piezo element vibration control signal configured to notice arrival.

FIG. 16 is a diagram illustrating one embodiment of the piezo element 200-3 vibration control signal configured to notice arrival.

The controller 380 may apply a voltage to the piezo element 230-2 to notice the user of the arrival of the smart shoe module 200 at the preset point of arrival, once the smart shoe module 200 reaches the preset point of arrival. A control signal for voltage application may be generated in the left and right smart shoe modules 200 three times simultaneously.

Figure 17:
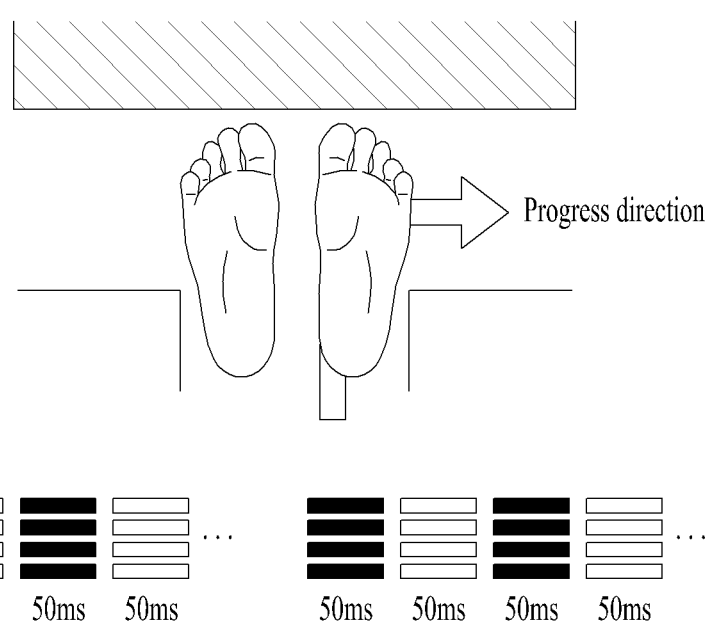
FIG. 17 is a diagram illustrating one embodiment of a piezo element vibration control signal configured to notice danger.

FIG. 17 is a diagram illustrating one embodiment of the piezo element 230-2 vibration control signal configured to notice danger.

When the location or location variation of the smart shoe modules 200 is processed along an unintended path or come near or reaches a dangerous point, the controller 380 may apply a voltage corresponding to a control signal configured to constantly generate a big vibration in the left and right smart shoe modules 200 at the same time.

Figure 18:
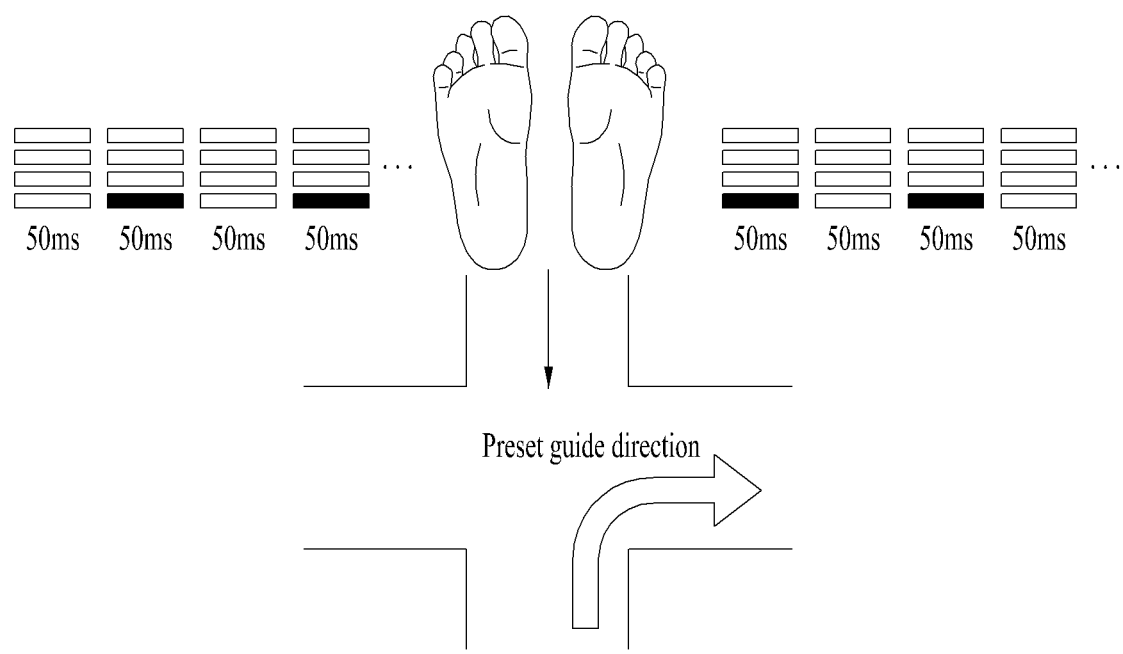
FIG. 18 is a diagram illustrating one embodiment of a piezo element vibration control signal configured to guide reverse motion.

FIG. 18 is a diagram illustrating one embodiment of the piezo element 230-2 vibration control signal configured to guide reverse motion.

If it is necessary to return in the reverse direction out of the route guidance, the controller 380 may apply a voltage corresponding to a control signal configured to continuously and alternately generate small vibrations in the left and right smart shoe modules 200.

Third Embodiment

Figure 19:
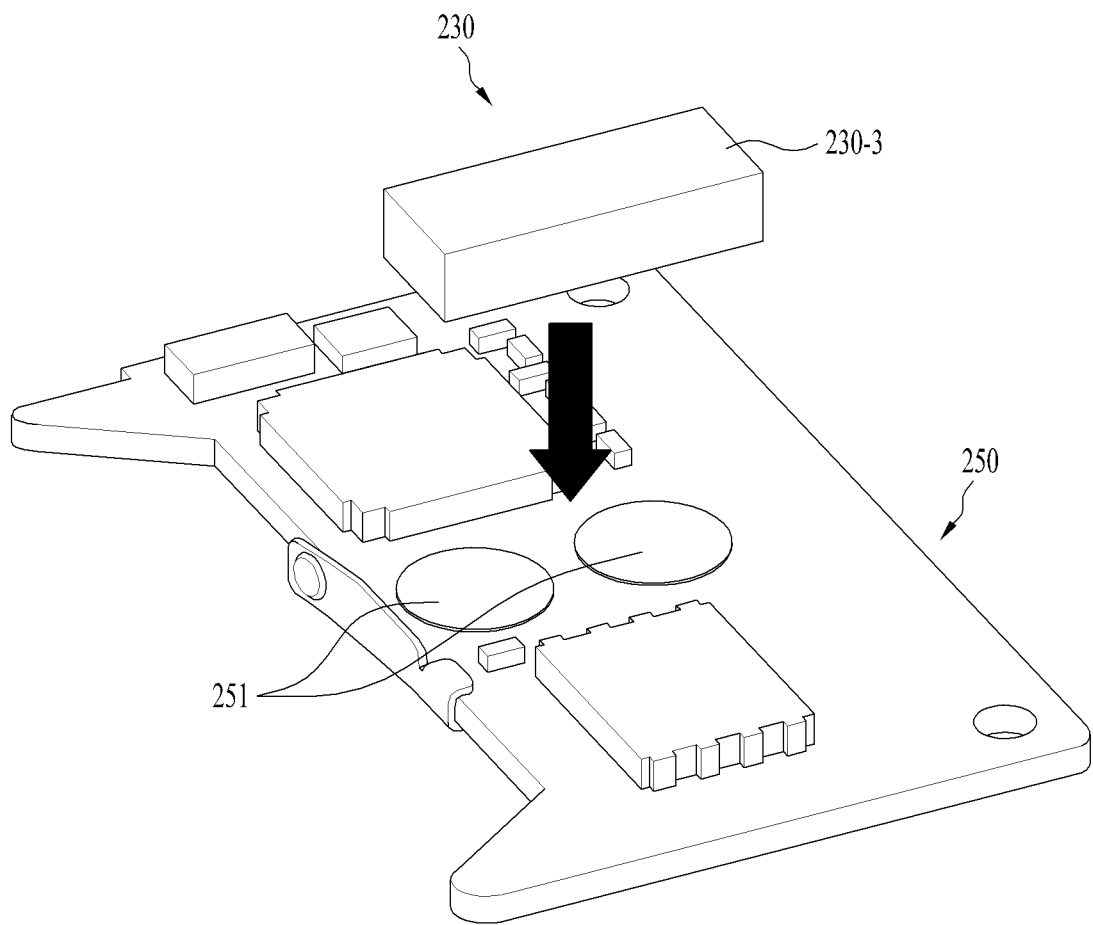
FIG. 19 is a diagram illustrating one embodiment when a dielectric material is used as the conductive member.

FIG. 19 is a diagram illustrating one embodiment when a dielectric material is used as the conductive member 230.

The conductive member 203 may be a dielectric material 230-3.

The dielectric material 230-3 may sense the variation of the capacitance generated by change of a gap between the dielectric material 230-3 and the first circuit unit 251 or a shape change of the dielectric material 230-3 according to the pressure applied to the dielectric material 230-3 and then measure a degree of the pressure.

In the smart shoe module in the neutral state, the dielectric material 230-3 may a preset gap with the first circuit unit 251 or contact with the first circuit unit 251. In the latter case, one surface of the dielectric material 230-3 may contact with the upper case 261 and the other surface may contact with the first circuit unit 251.

Alternatively, the dielectric material 230-3 is fixed to the circuit board 250, in contact with the first circuit unit 251, and it is spaced apart from the inner surface 2611 of the upper case 261.

A predetermined area of the first circuit unit 251 may be exposed to the surface of the circuit board 250. The first circuit unit 251 may be realized as Self Cap or Mutual Cap.

The controller (380, see FIG. 1) may measure the variation of the capacitance generated in the first circuit unit 251 of the smart shoe module 200 in the compression state.

Figure 20:
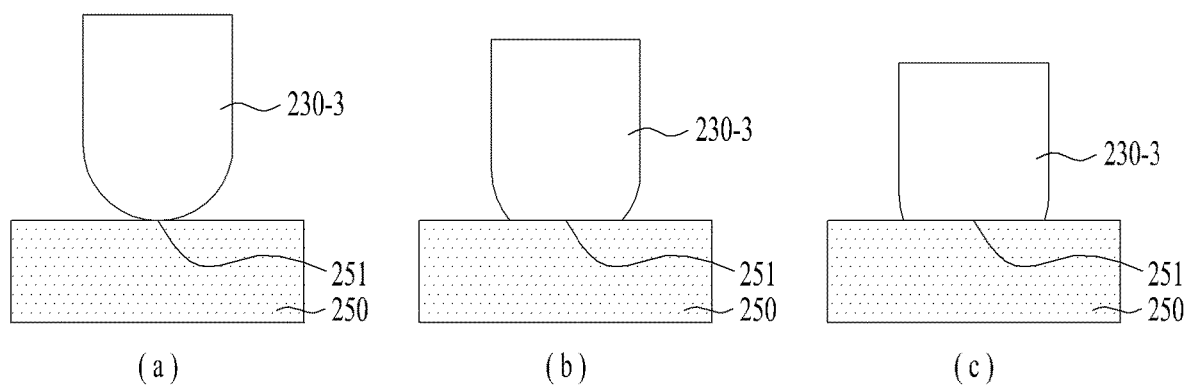
FIG. 20 is a schematic diagram illustrating a lateral surface of a smart shoe module including the dielectric material.

FIG. 20 is a schematic diagram illustrating a lateral surface of a smart shoe module 200 including the dielectric material 230-3.

FIGS. 20(a), 20(b) and 20 (c) illustrate that the dielectric material 230-3 is compressed in the first circuit unit 251 by the pressure sequentially.

The dielectric material 230-3 may have a cross sectional area which gradually decreases toward the first circuit unit 251 from the upper case 261.

As one example, the dielectric material 230-3 may have a cone shape. The cone-shaped dielectric material 230-3 may have an increasing contact area as the pressure applied to the smart shoe module 200 increases such that the capacitance variation may be generated. The controller (380, see FIG. 1) may figure out the capacitance variation and recognize whether the specific pressure value or more is activated on the smart shoe module 200.

The signal generation threshold pressure value provided as the specific pressure value may be designed to vary according to the dielectric permittivity and shape of the dielectric material 230-3.

Fourth Embodiment

Figure 21:
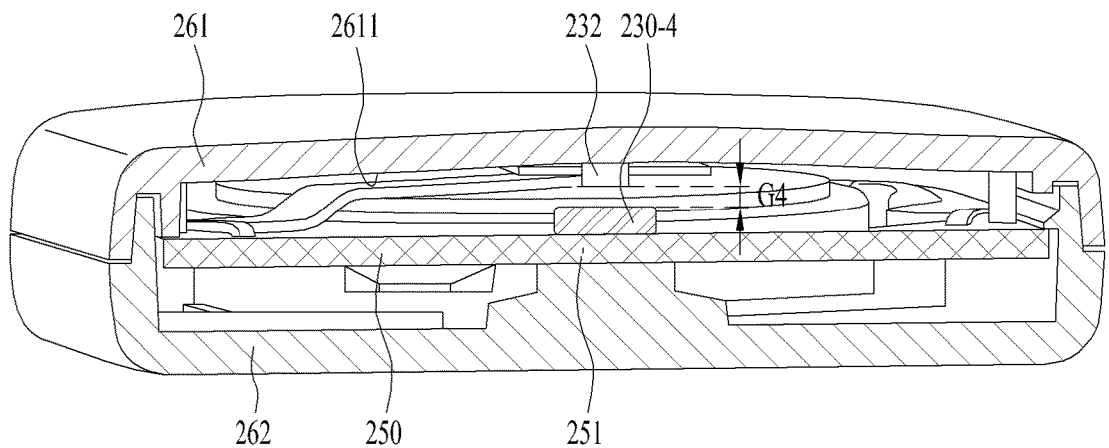
FIG. 21 is a diagram illustrating a further embodiment of the smart shoe module.

FIG. 21 is a diagram illustrating a further embodiment of the smart shoe module 200.

The conductive member 230 may include a dome cap 230-4 to form a dome switch type conductive member. In other words, the dome cap 230-4 may be loaded in the first circuit unit 251. The dome cap 230-4 may be fixed to the first circuit unit 251, not the upper case 261.

A key press unit 232 may be projected from the inner surface 2611 of the upper case 261 to be pressed smoothly.

When the specific pressure value or more is activated on the upper case 261 which is elastically movable, the dome cap 230-4 formed in the first circuit unit 251 is pressed to generate the on-signal in the smart shoe module 200.

The signal generation threshold pressure value may be variable according to the material or shape of the dome cap 230-4 and the fourth gap (G4) between the key press unit 232 and the dome cap 230-4.

Fifth Embodiment

Figure 22:
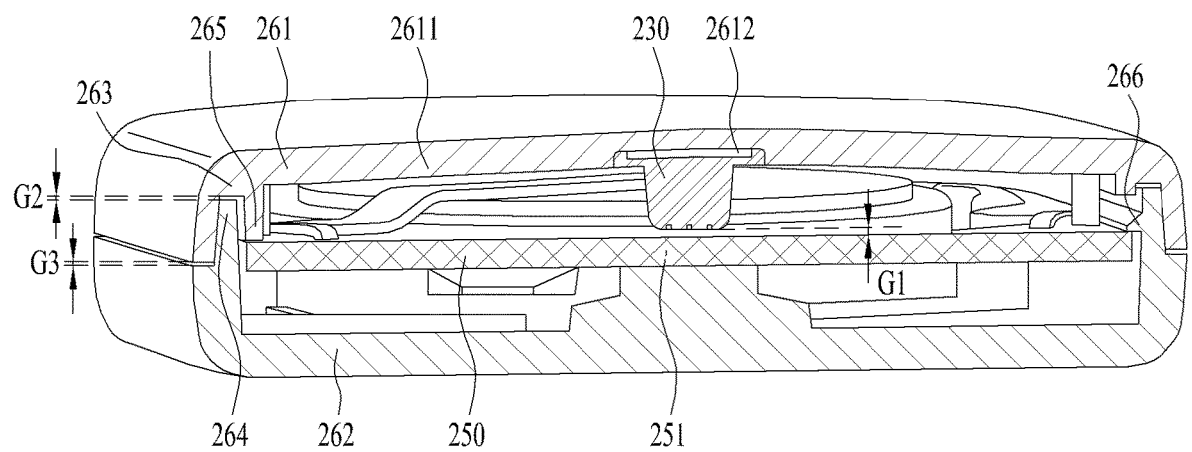
FIG. 22 is a diagram illustrating a still further embodiment of the smart shoe module.

FIG. 22 is a diagram illustrating a still further embodiment of the smart shoe module 200.

A first magnetic member 233 may be provided in the upper case 261 and a second magnetic member 234 configured to generate a repulsive force with respect to the first magnetic member 233 may be provided in the lower case 262.

When the load is continuously activated on the smart shoe module 200, deformation may occur in the housing 260 of the smart shoe module 200, in other words, the upper case 261 or the lower case 262 such that unintended change might occur in the signal generation threshold pressure value.

Accordingly, the change of the signal generation threshold pressure value may be minimized by using the first magnetic member 233 which is able to be kept semi-permanently and the repulsive force of the second magnetic member 234.

DESCRIPTION OF SPECIFIC EMBODIMENTS

Although embodiments have been described with reference to a number of illustrative embodiments thereof, it should be understood that numerous other modifications and embodiments can be devised by those skilled in the art that will fall within the spirit and scope of the principles of this disclosure.

More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

INDUSTRIAL APPLICABILITIES

Industrial applicability of the present invention is included in the description of the specific embodiments.

What is claimed is:

1. A smart shoe module comprising:
   an upper case provided to define an upper exterior of a pressure switch and configured to be elastically movable by a specific pressure value or more activating in a first direction;
   a lower case coupled to a lower end of the upper case and provided to define a lower end exterior of the pressure switch;
   a circuit board loaded in the lower case and comprising a first circuit unit;
   a conductive member provided between the upper case and the first circuit unit of the circuit board and configured to generate a signal in the first circuit unit according to the elastic motion; and
   a controller implemented to process the signal generated in the first circuit unit,
   wherein a first gap is formed in an outer boundary area of the coupling between the upper and the lower case.

2. The smart shoe module of claim 1, wherein the first circuit unit and the conductive member form a second gap.

3. The smart shoe module of claim 1, further comprising:
   a coupling hole provided in a predetermined area of one of the upper and lower cases;
   a coupling projection provided in a predetermined area of the other one and configured to be fitted to the coupling hole; and
   a support rib projected from an inner surface of the upper case and configured to support the first circuit unit,
   wherein a third gap is formed between the coupling hole and the coupling projection, and
   the support rib and the first circuit unit contact with each other.

4. The smart shoe module of claim 1, further comprising:
   a hook portion provided in the inner surface of the lower case and configured to fix the circuit board.

5. The smart shoe module of claim 1, further comprising:
   an adhesive tape provided between the conductive member and the upper case.

6. The smart shoe module of claim 1, wherein the conductive member is formed in the inner surface of the upper case by double-injection molding.

7. The smart shoe module of claim 6, further comprising:
   a recess portion formed in the inner surface of the upper case, corresponding to the conductive member.

8. The smart shoe module of claim 1, wherein the conductive member comprises at least one of a variable resistance element, a dielectric material and a dome cap.

9. The smart shoe module of claim 8, further comprising:
   a conductive layer configured to cover at least a predetermined area of an upper surface of the variable resistance element, when the conductive member is the variable resistance element.

10. A smart shoe module comprising:
    an upper case provided to define an upper exterior of a pressure switch and configured to be elastically movable by a specific pressure value or more activating in a first direction;
    a lower case coupled to a lower end of the upper case and provided to define a lower end exterior of the pressure switch;
    a circuit board loaded in the lower case and comprising a first circuit unit;
    a piezo element provided between the upper case and the first circuit unit of the circuit board and configured to generate a signal in the first circuit unit according to the elastic motion; and
    a controller implemented to process the signal generated in the first circuit unit,
    wherein the controller calculates a user's momentum based on a voltage of a signal generated in the first circuit unit.

11. The smart shoe module of claim 10, further comprising:
    a power supply unit configured to be supplied electricity generated in the piezo element and have the electricity accumulative therein.

12. The smart shoe module of claim 10, further comprising:
    a power supply unit configured to apply a voltage to the piezo element,
    wherein the controller controls the power supply unit to apply a corresponding voltage to a control signal preset in the piezo element.

13. The smart shoe module of claim 12, wherein the preset control signal is configured to vary at least one of an applied voltage size, frequency and period.

14. The smart shoe module of claim 12, further comprising:
a location information module configured to measure or transmit location information about the smart shoe module,
wherein the controller varies a period of the applied voltage in response to the location information measured by the location information module and a distance with a specific location.

15. The smart shoe module of claim 12, comprising:
a left smart shoe module and a right smart shoe module which include the piezo elements, respectively,
wherein the preset control signal comprises,
a first control signal configured to apply a voltage to one of the piezo elements;
a second control signal configured to apply voltages to both of the piezo element; and
a third control signal configured to alternately apply voltages to the piezo elements.

16. A smart shoe module system comprising:
a left smart shoe module and a right smart shoe module,
wherein each of the left and right smart shoe modules comprises,
an upper case provided to define an upper exterior of a pressure switch and configured to be elastically movable by a specific pressure value or more activating in a first direction;
a lower case coupled to a lower end of the upper case and provided to define a lower end exterior of the pressure switch;
a circuit board loaded in the lower case and comprising a first circuit unit;
a conductive member configured to form a first gap in the upper case, together with the first circuit unit, and generate a signal in the first circuit unit according to the elastic motion;
a motion sensor comprising an acceleration sensor and a gyro sensor; and
a controller implemented to process the signal generated in the first circuit unit,
wherein the controller is configured to calibrate a rate of on-signals measured by the first circuit unit provided in each of the left and right smart shoe modules to a calibrated on-signal rate, based on a rate of a ground supporting time analyzed by each of the motion sensors.

17. The smart shoe module system of claim 16, wherein the controller activates the motion sensor which is in inactivated state, when performing the calibration.

18. The smart shoe module system of claim 16, wherein the controller performs the calibration at preset intervals or intervals set by the user.

* * * * *